US012779034B2

(12) United States Patent
Liu et al.

(10) Patent No.: US 12,779,034 B2
(45) Date of Patent: Nov. 3, 2026

(54) SELF-SUSTAINED RELEASE IMMUNE ADJUVANT SUSPENSION, PREPARATION METHOD THEREFOR, AND USE THEREOF

(71) Applicant: INNOBM PHARMACEUTICALS CO., LTD., Suzhou (CN)

(72) Inventors: Zhuang Liu, Suzhou (CN); Huiquan Tao, Suzhou (CN); Zhongqing Deng, Suzhou (CN); Yuchen Wu, Suzhou (CN); Shang Bai, Suzhou (CN); Xuanfang Zhou, Suzhou (CN)

(73) Assignee: INNOBM PHARMACEUTICALS CO., LTD., Suzhou (CN)

( * ) Notice: Subject to any disclaimer, the term of this patent is extended or adjusted under 35 U.S.C. 154(b) by 432 days.

(21) Appl. No.: 18/265,987

(22) PCT Filed: Dec. 30, 2021

(86) PCT No.: PCT/CN2021/143057
§ 371 (c)(1),
(2) Date: Jun. 8, 2023

(87) PCT Pub. No.: WO2022/143894
PCT Pub. Date: Jul. 7, 2022

(65) Prior Publication Data

US 2024/0050560 A1 Feb. 15, 2024

(30) Foreign Application Priority Data

Dec. 30, 2020 (CN) ........................ 202011612051.1
Nov. 5, 2021 (CN) ........................ 202111307908.3

(51) Int. Cl.

| | |
|---|---|
| ***A61K 39/39*** | (2006.01) |
| ***A61K 9/10*** | (2006.01) |
| ***A61K 39/00*** | (2006.01) |
| ***A61K 47/26*** | (2006.01) |
| ***A61K 47/34*** | (2017.01) |
| ***A61K 47/44*** | (2017.01) |
| ***A61P 37/04*** | (2006.01) |

(52) U.S. Cl.
CPC ................ *A61K 39/39* (2013.01); *A61K 9/10* (2013.01); *A61K 47/26* (2013.01); *A61K 47/34* (2013.01); *A61K 47/44* (2013.01); *A61P 37/04* (2018.01); *A61K 2039/55511* (2013.01); *A61K 2039/55572* (2013.01)

(58) Field of Classification Search
None
See application file for complete search history.

(56) References Cited

U.S. PATENT DOCUMENTS

2007/0264317 A1 11/2007 Yosha et al.

FOREIGN PATENT DOCUMENTS

| | | | | |
|---|---|---|---|---|
| CN | 101129373 A | 2/2008 | | |
| CN | 101909664 A | 12/2010 | | |
| CN | 103202803 A | 7/2013 | | |
| CN | 108187040 A | 6/2018 | | |
| CN | 110430868 A | 11/2019 | | |
| CN | 110917345 A | * | 3/2020 | ............. A61K 45/06 |
| KR | 101647299 B1 | 8/2016 | | |
| WO | 2008/147489 A1 | 12/2008 | | |

OTHER PUBLICATIONS

Rejection Decision received for Chinese Patent Application No. 202011612051.1, mailed on Nov. 20, 2025, 14 Pages.
"Notice of Second Review Opinion" for CN Application No. 202011612051.1, issued on Jul. 9, 2025, 12 Pages.
"Supplementary Retrieval Report" for CN Application No. 202011612051.1, Jul. 8, 2025, 4 Pages.
"New Technology and Product Development for Pharmaceutical Preparations", edited by Hong Yi, Huazhong University of Science and Technology Press, Nov. 30, 2020. 8 Pages.
International Search Report and Written Opinion received for International Patent Application No. PCT/CN2021/143057, mailed Mar. 30, 2022, 12 pages.
First Office Action received for CN Application No. 202011612051.1, mailed on May 9, 2023, 18 Pages including English translation.
First Office Action received for CN Application No. 202111307908.3, mailed on Jun. 1, 2022, 13 Pages including English translation.

(Continued)

*Primary Examiner* — Melissa S Mercier
(74) *Attorney, Agent, or Firm* — Harmohinder S. Bedi

(57) ABSTRACT

The present application relates to a self-sustained release immune adjuvant suspension comprising microparticles composed of a lipid soluble immune adjuvant and a surfactant, the balance being a dispersant, wherein the lipid soluble immune adjuvant is coated with the surfactant to form the microparticles which are dispersed in the dispersant to form a suspension. The self-sustained release immune adjuvant suspension can be retained in a tumor for a long time and can maintain a sustained release property, and can also inhibit the growth of distal metastatic tumors and reduce the probability of tumor recurrence by means of an immune response. The present application further provides a preparation method for a self-sustained release immune adjuvant suspension, and use of the self-sustained release immune adjuvant suspension in a sensitizing formulation used for tumor therapies, such as, radiotherapy, chemotherapy, or thermotherapy.

5 Claims, 9 Drawing Sheets

(56) References Cited

OTHER PUBLICATIONS

"Preparation of nanosuspensions", edited by Pan Weisan, Industrial Pharmacy, Beijing: China Pharmaceutical Science and Technology Press, 3rd edition, p. 84, public date Aug. 31, 2015.
Chollet, J.L. et al., "Development of a topically active imiquimod formulation.", Pharmaceutical Development and Technology., vol. 4, No. 1, pp. 35-43, Dec. 31, 1999.
Second Office Action received for CN Application No. 202111307908.3, mailed on Aug. 30, 2022, 15 Pages Including English translation.
Zhang Shuren, "Chinese Journal of Cancer Prevention and Treatment", vol. 23, Issue 18, Sep. 2016, 8 Pages.

* cited by examiner

In-Vitro Release of Doxorubicin (DOX)

In-Vitro Release of Doxorubicin (DOX)

SELF-SUSTAINED RELEASE IMMUNE ADJUVANT SUSPENSION, PREPARATION METHOD THEREFOR, AND USE THEREOF

RELATED APPLICATION

This application is a National Stage Application of International Application No. PCT/CN2021/143057 filed on Dec. 30, 2021 and claims priority from CN application No. 202111307908.3 filed on Nov. 5, 2021, and CN application No. 202011612051.1 filed on Dec. 30, 2020 which are hereby expressly incorporated by reference in their entirety for all purposes.

1. FIELD OF THE INVENTION

The present application relates to the field of biomedicine, in particular to a self-sustained release immune adjuvant suspension, a preparation method therefor and a use thereof.

2. BACKGROUND TECHNIQUE

Chemotherapy, radiotherapy, and microwave thermal ablation are effective methods for the treatment of malignant tumors, which have played a great role in the clinical treatment of tumors and have been widely used in common tumors such as liver cancers, lung cancers, and kidney cancers. Radioactive therapy (briefly, radiotherapy), a ray-based external radiation therapy, is widely used in clinic. However, it is a local therapeutic regimen by which only local tumors can be radiated, and the distal metastatic tumors (e.g., distal occult tumors) cannot be effectively radiated. The external radiation radiotherapy widely used in clinic is to perform a locally targeted radiation on the tumor site with a ray (e.g., an X ray) to achieve the goal of killing tumor cells, or even have an opportunity to achieve healing in the case that the tumor does not undergo a distal metastasis. However, in the case that the tumor has underwent a distal metastasis, it is difficult to cover all the tumor cells, especially the metastatic tumor cells, in the human body by means of local therapy, and the "fishes escaping out of the net" are likely to grow a new tumor metastasis lesion at a distal site.

In the clinical application of radiotherapy, it is found that an "abscopal effect" may occur in a small number of patients, that is, a local treatment on tumors may sometimes inhibit the growth of distal tumors which are not radiated. Recently, such "abscopal effect" induced by radiotherapy has aroused a great interest of researchers. Studies have shown that the mechanism of "abscopal effect" relies on inducing the immunogenic cell death of tumor cells, exposing the tumor-associated antigens to activate an immune response against tumors, and further achieving an immunosuppression of distal tumors through the infiltration of tumor-specific CD8+ T cells to the distal tumors. Although the induced "abscopal effect" is of important significance in clinic, this effect has huge individual differences. For a majority of clinical patients, the "abscopal effect" induced by radiotherapy is not highly significant. An important reason is that the tumor-associated antigens in the tumor cell "corpses" produced by inducing the immunogenic cell death of tumor cells itself is not highly immunogenic, and cannot serve as an effective "tumor vaccine". In most cases, it is difficult to activate an effective anti-tumor immune response.

In modern medical technologies, an effective immune response requires a sufficient exposure of tumor antigen and an antigen presentation of immune adjuvant, wherein the effect of the immune adjuvant is to exponentially amplify the immune response produced by the tumor antigen through the stimulation of immune cells. Therefore, if an immune adjuvant is locally injected into a tumor during the treatment of tumor, and then the tumor is further treated, it is expected to significantly amplify the immunogenicity of the tumor-associated antigen produced after radiotherapy by the immune stimulation effect of the adjuvant, such as, recruiting antigen presenting cells to the site of tumor residues to recognize, phagocytize and present the tumor antigens, so as to produce an endogenous "tumor vaccine" in vivo to obtain a strong anti-tumor immune response and achieve a more effective inhibition on the distal tumors.

Since most clinical radiotherapies are radiations with multiple sub-doses, it is required that the injected immunostimulants can be retained in the tumor for a long time and sustainedly released, which is vital for the sensitization of radiotherapy. At present, the problem of most water-soluble immune adjuvants themselves are easy to be cleared via blood circulation, and cannot be retained in the action site for a long time to achieve a long-acting stimulation; while lipid soluble immune adjuvants have a poor dispersibility and are difficult to use directly. How to design immunostimulants properly, how to design an operable production method, and how to achieve the sterilization and the long-term storage stability of the pharmaceutical products are all problems. For example, during the preparation of micro- to nano-particles by a ball milling process, the produced ceramic particles are likely to remain in the product. Such impurities are not problematic in the preparation process of common micro- to nano-materials, but are riskier for use in human injection. These unsolved problems in the drug preparation result in that many experimental drugs cannot be truly applied in clinic.

Imiquimod, currently approved for clinical use, is a typical lipid soluble immune adjuvant. This imidazoquinolinamine micromolecular immunomodulator is not a cytotoxic drug, and has no obvious effect of directly killing viruses or tumor cells. Imiquimod is a ligand of the Toll-like receptor 7 (TLR7), which is capable of stimulating macrophages, monocytes and dendritic cells, inducing the generation of interferon α (IFN-α) and tumor necrosis factor α (TNF-α), while stimulating the generation of cytokines such as interleukin-2 (IL-2), IL-6, IL-8, etc., thereby further stimulating the activation of cellular immunity, recognizing viruses or other tumor antigens, activating the associated immune responses, and eliminating the pathogenic factors.

At the present stage, a mature dosage form of imiquimod is cream formulation, which is often applied onto the epidermal lesion regions for the clinical treatment of diseases caused by topical virus infection such as condyloma acuminatum, and has also been tried in clinic trials for the treatment of superficial skin tumors. Currently, imiquimod has been approved for use in the treatment of head and neck actinic keratosis and superficial basaloma. In addition, many clinical trials have confirmed that imiquimod plays a role of immune adjuvant in the treatment of superficial tumors such as squamous cell carcinoma, metastatic melanoma, and vulvar intraepithelial neoplasia, and has an application potential.

However, imiquimod itself is a lipid soluble micromolecule which is hardly soluble in water. At the same time, imiquimod has a relatively strong skin irritation. By applying a 5% imiquimod cream onto the naked skin of mice, a mouse model of psoriatic lesion can be established, that is enough to explain the irritation of imiquimod to normal tissues. External administration has both advantages and disadvantages. Although it has a good immune-enhancing effect in the immunotherapy of individual superficial lesions, it also limits the immunotherapeutic use of imiquimod in other tumors.

At present, there are primarily two methods for preparing an imiquimod-containing injectable solution: one involves directly dissolving imiquimod into an acid, for example, dissolving imiquimod into hydrochloric acid to form a hydrochloride which is dispersed in an aqueous phase. However, the solution obtained by this method has a relatively low pH, typically around 3.0-4.0, which is a little irritative when used in organisms. In addition, the imiquimod hydrochloride as micromolecule will quickly seep from the tumor to the blood after injection, so that it has a relatively high acute exposure in blood (causing a safety risk). At the same time, the imiquimod hydrochloride has a very short half-life in tumors and will be quickly cleared so that its immune activation effect after intratumoral administration cannot be maintained for a long time.

Another method for preparing an injectable solution of imiquimod is to load R837 onto an amphiphilic polymer or other nanostructures capable of loading a hydrophobic drug. However, the preparation process for such nano-particles is often complicated, and not conducive to the process scale-up and standardized batch production. In addition, these nanoparticle formulations are often difficult to stably exist under the condition of terminal high-temperature and high-pressure sterilization (according to the Guiding Principles for Research and Verification of Sterilization and Aseptic Processes of Chemical Injections, the terminal high-temperature and high-pressure sterilization is the preferred sterilization strategy for injections).

Further application of similar lipid soluble immune adjuvants faces similar problems. Therefore, it is of great significance to develop an injectable lipid soluble immune adjuvant formulation as the immune adjuvant for use in the immunotherapy of non-superficial tumors. Such formulations should achieve a long-term retention and a sustained release in tumors, and have reduced exposure in blood and normal tissues so as to ensure the safety in clinical use. In addition, to meet the requirement of industrialization, it is required that the preparation method for such formulations can be scaled up, and the stability of the formulation can meet the requirement of the terminal high-temperature and high-pressure sterilization.

SUMMARY OF THE INVENTION

The present application provides a self-sustained release immune adjuvant suspension composed of a lipid soluble immune adjuvant and a surfactant, the remaining components being a dispersing medium, wherein the lipid soluble immune adjuvant is coated with the surfactant to form microparticles which are dispersed in the dispersing medium to form the suspension.

In some embodiments, the lipid soluble immune adjuvant comprises at least one of imiquimod (R837), resiquimod (R848) or glucopyranoside lipid A (MPLA).

In some embodiments, the particles of the lipid soluble immune adjuvant are core-shell composite particles with a particle size of 0.5 to 5 microns.

In some embodiments, the core-shell composite microparticles of the lipid soluble immune adjuvant have a particle size of 1 to 2 microns.

In some embodiments, the lipid soluble immune adjuvant is imiquimod microparticles.

In some embodiments, the imiquimod microparticles have an average particle size of 0.5 to 5 microns.

In some embodiments, the surfactant is a surfactant with a higher fatty acid chain.

In some embodiments, the surfactant with a higher fatty acid chain comprises an anionic surfactant.

In some embodiments, the anionic surfactant comprises at least one of sodium oleate, sodium dodecyl sulfate, sodium stearate, sodium N-lauroyl sarcosinate, sodium cocoyl methyl taurate, sodium N-lauroyl glutamate, sodium lauryl polyoxyethylene ether carboxylate, and dodecyl phosphate.

In some embodiments, the surfactant with a higher fatty acid chain comprises an amphiphilic ionic surfactant.

In some embodiments, the surfactant with a higher fatty acid chain comprises a phospholipid ionic surfactant.

In some embodiments, the phospholipid ionic surfactant comprises at least one of lecithin, soybean phospholipid, phosphatidylglycerol, phosphatidylethanolamine, phosphatidylserine, and phosphatidylinositol.

In some embodiments, a hydrophobic structural moiety of the surfactant comprises not less than 20 oxypropylene units.

In some embodiments, the surfactant comprises at least one of Poloxamer 188, Poloxamer 237, Poloxamer 338, and Poloxamer 407.

In some embodiments, a hydrophobic structural moiety of the surfactant comprises one or more hydrocarbon chains with a total of not less than 15 carbon atoms.

In some embodiments, the surfactant comprises at least one of sorbitan sesquioleate, soybean phospholipid, glyceryl monostearate, polysorbate 40, polysorbate 60, polysorbate 65, polysorbate 80, polysorbate 85, sorbitan stearate (Span 60), stearate, vitamin E polyethylene glycol succinate, polyoxyethylene alkyl ether, polyoxyethylene stearate, polyoxyl (40) stearate, sucrose stearate, a polyoxyethylenated castor oil derivative, cetomacrogol 1000, or lecithin.

In some embodiments, the surfactant is a mixture of two surfactants with different hydrophilic-lipophilic balance values.

In some embodiments, the self-sustained release immune adjuvant suspension comprises an imiquimod suspension formulation comprising: imiquimod microparticles, surfactant with a higher fatty acid chain and a dispersing medium.

In some embodiments, in the imiquimod suspension, the concentration of the imiquimod microparticles is 1 to 18 mg/mL, and a mass ratio of the surfactant with a higher fatty acid chain to the imiquimod microparticles is 0.025 to 3:1.

In some embodiments, in the imiquimod suspension, a mass ratio of the surfactant with a higher fatty acid chain to the imiquimod microparticles is 0.1 to 1:1.

In another aspect, the present application provides a preparation method for a self-sustained release immune adjuvant suspension comprising the steps of: S1: dispersing a surfactant and a lipid soluble immune adjuvant in a single dispersing system, and stirring to obtain a suspension; S2: processing the prepared suspension by homogenization/high-shear process; and S3: sterilizing the homogenized/high-shear-processed suspension.

In some embodiments, the preparation method comprises: S1: forming primary micron-sized powder by air jet pulverization process of the lipid soluble immune adjuvant; S2: adding an aqueous solution of surfactant into the primary micron-sized powder of the lipid soluble immune adjuvant obtained in the step S1 at a mass ratio (1:0.025 to 5) of the lipid soluble immune adjuvant to the surfactant, performing a high-pressure homogenization process, and removing homogenate after the processing; or S2': adding an aqueous solution of surfactant into the primary micron-sized powder of the lipid soluble immune adjuvant obtained in the step S1 at a mass ratio (1:0.025 to 5) of the lipid soluble immune adjuvant to the surfactant, performing a high-shear process, and removing homogenate after the processing; and S3: sterilizing at high pressure.

In some embodiments, in the step S2 of the preparation method, the surfactant comprises two surfactants with different solubility.

In some embodiments, the high-pressure sterilization is performed at 105° C. to 150° C. for 10 to 20 min.

In another aspect, the present application further provides a preparation method for an imiquimod suspension formulation comprising the steps of: S1: dispersing a surfactant with a higher fatty acid chain and imiquimod microparticles in a single dispersing system, and stirring to obtain a suspension; S2: homogenizing the prepared suspension; and S3: packaging the homogenized suspension, sealing, and sterilizing at high temperature and high pressure. In some embodiments, the high-temperature and high-pressure sterilization is performed at 110° C. to 145° C. for 5 to 30 min.

In another aspect, the present application further provides use of the self-sustained release immune adjuvant suspension obtained by the preparation method of the present application in preparation of an auxiliary therapeutic medicament for tumors.

In another aspect, the present application further provides a self-sustained release immune adjuvant composition comprising a first composition and a second composition, wherein the first composition is composed of a lipid soluble immune adjuvant and a surfactant, the remaining components being a dispersant, wherein the lipid soluble immune adjuvant is coated with the surfactant to form microparticles which are dispersed in the dispersant to form a suspension; and the second composition comprises lyophilized powder formed from a soluble alginate and a protective filler.

In some embodiments, in the self-sustained release immune adjuvant composition, the lipid soluble immune adjuvant comprises at least one of imiquimod (R837), resiquimod (R848) or glucopyranoside lipid A (MPLA).

In some embodiments, in the self-sustained release immune adjuvant composition, a hydrophobic structural moiety of the surfactant comprises not less than 20 oxypropylene units.

In some embodiments, in the self-sustained release immune adjuvant composition, the surfactant comprises at least one of Poloxamer 188, Poloxamer 237, Poloxamer 338, and Poloxamer 407.

In some embodiments, in the self-sustained release immune adjuvant composition, a hydrophobic structural moiety of the surfactant comprises one or more hydrocarbon chains with a total of not less than 15 carbon atoms.

In some embodiments, in the self-sustained release immune adjuvant composition, the surfactant comprises at least one of sorbitan sesquioleate, soybean phospholipid, glyceryl monostearate, polysorbate 40, polysorbate 60, polysorbate 65, polysorbate 80, polysorbate 85, sorbitan stearate (Span 60), stearate, vitamin E polyethylene glycol succinate, polyoxyethylene alkyl ether, polyoxyethylene stearate, polyoxyl (40) stearate, sucrose stearate, a polyoxyethylenated castor oil derivative, cetomacrogol 1000, or lecithin.

In some embodiments, in the self-sustained release immune adjuvant composition, the surfactant is a mixture of two surfactants with different hydrophilic-lipophilic balance values.

In some embodiments, in the self-sustained release immune adjuvant composition, the dispersant is water or normal saline.

In some embodiments, in the self-sustained release immune adjuvant composition, the protective filler is mannitol or lactose.

In some embodiments, the second composition further comprises a pH regulator.

In another aspect, the present application further provides use of the self-sustained release immune adjuvant suspension or the self-sustained release immune adjuvant composition in preparation of an anti-tumor combinational immunotherapeutic formulation.

In some embodiments, the self-sustained release immune adjuvant comprises an imiquimod suspension formulation.

In some embodiments, the imiquimod suspension formulation is pre-mixed with a platinum-based chemotherapeutic drug to assist a sustained release of the platinum-based chemotherapeutic drug.

In some embodiments, the imiquimod suspension formulation is pre-mixed with an anthracycline-based chemotherapeutic drug to assist a sustained release of the anthracycline-based chemotherapeutic drug.

In another aspect, the present application further provides use of the self-sustained release immune adjuvant suspension or the self-sustained release immune adjuvant composition in preparation of a radiotherapy sensitizing agent.

In another aspect, the present application further provides use of the self-sustained release immune adjuvant suspension or the self-sustained release immune adjuvant composition in preparation of a chemotherapy sensitizing agent.

In another aspect, the present application further provides use of the self-sustained release immune adjuvant suspension or the self-sustained release immune adjuvant composition in preparation of a thermotherapy sensitizing agent.

In another aspect, the present application further provides use of the self-sustained release immune adjuvant suspension or the self-sustained release immune adjuvant composition in preparation of an ethanol ablation sensitizing agent.

Persons skilled in the art can readily recognize other aspects and advantages of the present application from the detailed description below. The following detailed description only shows and describes exemplary embodiments of the present application. As persons skilled in the art will appreciate, the present application enables persons skilled in the art to make modifications to the disclosed embodiments without departing the spirit and scope of the application involved in the present application. Correspondingly, the accompany drawings and description in the specification of the present application are only illustrative, rather than restrictive.

BRIEF DESCRIPTION OF THE DRAWINGS

The specific features of the application involved in the present application are as shown in the appended claims. By referring to the exemplary embodiments as detailedly described below and the accompanying drawings, the features, and advantages of the application involved in the present application can be better understood. The accompany drawings are briefly described as follows:

DETAILED DESCRIPTION OF THE INVENTION

Figure 1:
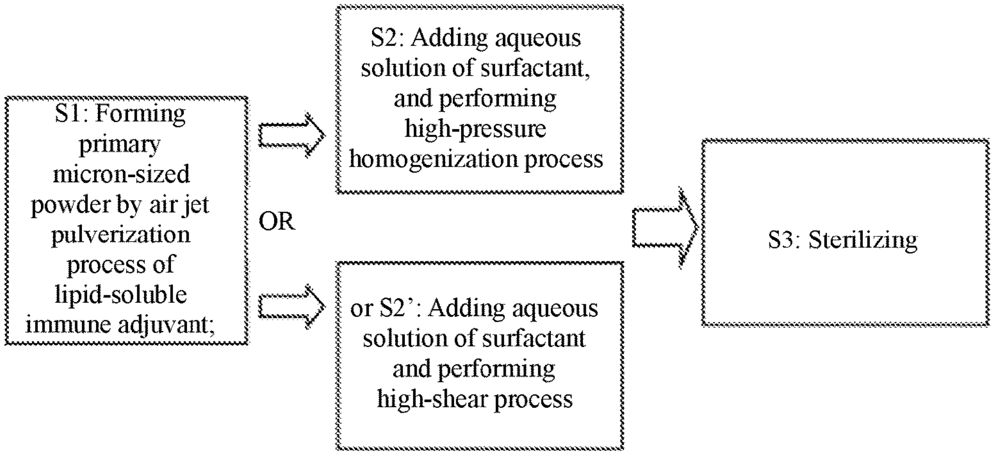
FIG. 1 is a schematic view showing the preparation of a self-sustained release immune adjuvant suspension.

Here in after the embodiments of the application of the application are described by specific examples. Those skilled in the art can easily understand other advantages and effects of the application as described in the present application from the disclosure in the description.

DETAILED DESCRIPTION

The present application provides a self-sustained release immune adjuvant suspension, which is a novel immune adjuvant dosage form having a good in-situ dispersion effect and capable of achieving a self-sustained release to assist in chemotherapy, radiotherapy or thermotherapy so as to generate an immune memory and activate human immune characteristics, and an anti-cancer pharmaceutical composition reducing the probability of cancer metastasis and recurrence, which can inhibit and reduce the probability of growth and tumor recurrence of a distal metastatic tumor by means of an immune response while effectively killing an in-situ tumor.

To address the related technical problems, the present application provides the following solutions:

A self-sustained release immune adjuvant suspension composed of a lipid soluble immune adjuvant and a surfactant, the balance being a dispersant, wherein the lipid soluble immune adjuvant is coated with the surfactant to form microparticles which are dispersed in the dispersant to form a suspension.

Further, the dispersant is water or normal saline.

Further, the lipid soluble immune adjuvant comprises at least one of imiquimod (R837), resiquimod (R848) or glucopyranoside lipid A (MPLA).

Further, a hydrophobic structural moiety of the surfactant comprises not less than 20 oxypropylene units; in particular, including Poloxamer 188 (P188), Poloxamer 237, Poloxamer 338, Poloxamer 407.

Alternatively, the hydrophobic structural moiety of the surfactant comprises one or more hydrocarbon chains with not less than 15 carbon atoms; in particular, including at least one of sorbitan sesquioleate, soybean phospholipid, glyceryl monostearate, polysorbate 40, polysorbate 60, polysorbate 65, polysorbate 80, polysorbate 85, sorbitan stearate (Span 60), stearate, vitamin E polyethylene succinate, polyoxyethylene alkyl ether, polyoxyethylene stearate, polyoxyl (40) stearate, sucrose stearate, a polyoxyethylenated castor oil derivative, cetomacrogol 1000, or lecithin.

Further, the self-sustained release immune adjuvant suspension is composite particles with a particle size of 0.5 to 5 microns, wherein the lipid soluble immune adjuvant is coated with the surfactant. Preferably, the self-sustained release immune adjuvant suspension has a particle size of 1 to 2 microns.

Further alternatively, the surfactant can be a mixture of two surfactants with different hydrophilic-lipophilic balance values (HLB values). The two surfactants with different hydrophilic-lipophilic balance values can operate in a manner that after the composite particles enter the tumor, the surfactant with a higher HLB value is first dissolved, and some openings or minor defect areas are thus formed on the coated surface of the lipid soluble immune adjuvant microparticles, so that the surface area of the inner imiquimod microparticles varies gradually, and the active ingredients is gradually released. Further, a more personalized medicament scheme can be formulated via the ratio of the two surfactants in accordance with the practical requirement of different tumors and human bodies.

The present application provides a preparation method for a self-sustained release immune adjuvant suspension characterized by comprising the steps of:

S1: forming primary powder by air jet pulverization process of the lipid soluble immune adjuvant;

S2: adding an aqueous solution of surfactant into the primary powder obtained in the step S1, performing a high-pressure homogenization process, and removing homogenate after the processing;

or S2': adding an aqueous solution of surfactant into the primary powder obtained in the step S1, performing a high-shear process, and removing homogenate after the processing; and S3: sterilizing.

Further, the aqueous surfactant solution in the step S1 comprises two surfactants with different hydrophilic-lipophilic balance values.

Preferably, the aqueous surfactant solution in the step S1 has a concentration of 6 to 30 mg/mL.

Further, the sterilizing in the step S3 is a heat-moisture treatment performed at 105° C. to 150° C. for 10 to 15 min.

The present application further provides a self-sustained release immune adjuvant composition comprising a first composition and a second composition, wherein the first composition is composed of a lipid soluble immune adjuvant and a surfactant, the balance being a dispersant, wherein the lipid soluble immune adjuvant is coated with the surfactant to form microparticles which are dispersed in the dispersant to form a suspension; and the second composition comprises lyophilized powder formed from a soluble alginate and a protective filler.

The second composition can further optimize the sustained-release characteristic of the first composition.

Further, the dispersant is water or normal saline.

Further, the lipid soluble immune adjuvant comprises at least one of imiquimod (R837), resiquimod (R848) or glucopyranoside lipid A (MPLA).

Further, the hydrophobic structural moiety of the surfactant comprises not less than 20 oxypropylene units, including Poloxamer 188, Poloxamer 237, Poloxamer 338, Poloxamer 407; or including one or more hydrocarbon chains with not less than 15 carbon atoms; in, comprises a including at least one of sorbitan sesquioleate, soybean phospholipid, glyceryl monostearate, polysorbate 40, polysorbate 60, polysorbate 65, polysorbate 80, polysorbate 85, sorbitan stearate (Span 60), stearate, vitamin E polyethylene glycol succinate, polyoxyethylene alkyl ether, polyoxyethylene stearate, polyoxyl (40) stearate, sucrose stearate, a polyoxyethylenated castor oil derivative, cetomacrogol 1000, or lecithin.

The present application further provides use of the self-sustained release immune adjuvant suspension in preparation of a radiotherapy sensitizing agent.

The present application further provides use of the self-sustained release immune adjuvant suspension in preparation of a chemotherapy sensitizing agent.

The present application further provides use of the self-sustained release immune adjuvant suspension in preparation of a thermotherapy sensitizing agent.

Using the technical solutions of the present application, the following beneficial effects can be provided:

The self-sustained release immune adjuvant suspension of the present application is a suspension composed of the lipid soluble immune adjuvant microparticles, and the lipid soluble immune adjuvant surface is coated with a surfactant. As compared with the hydrochloride salt of the immune adjuvant or other water-soluble immune adjuvant molecules (such as, CpG, polyIC), no other sustained-release auxiliary agent is needed after local injection of the present formulation, namely, it can be retained in the tumor and sustainedly released to produce a self-sustained release effect so that the immunostimulant effect is stable and long-lasting. Since most clinical radiotherapies are radiations with multiple sub-doses (e.g., radiations five times in a week), it is required that the injected immunostimulant can be retained in the tumor for a longer time and sustainedly released, which can effectively enhance the induced immunogenic cell death, and induce an anti-tumor immune response. The long-term retention and sustained release of the presently formulated imiquimod microparticles in the tumor are vital to the sensitization of the radiotherapy, chemotherapy or thermotherapy and the induction of the anti-tumor immune response.

The self-sustained release immune adjuvant suspension of the present application overcomes the technical problem that the lipid soluble immune adjuvant itself has a poor water solubility, while the hydrochloride salt of the lipid soluble immune adjuvant as micromolecule will rapidly diffuse to other organs and be metabolized out of the body when injected into the tumor, even if it has a good water solubility. A micron-sized suspension made from the lipid soluble immune adjuvant is a novel dosage form of lipid soluble immune adjuvant with self-sustained release effect, which increases the retention time of the lipid soluble immune adjuvant microparticles in the tumor and slows down the release of the immune adjuvant molecules. Such characteristic is vital to the sensitization of external radiation radiotherapy. In addition, since the micron-sized particle suspension is required to undergo a standard high-pressure sterilization operation to meet the sterile requirement prior to injection into the tumor, it is necessary to ensure that the microparticles would not agglomerate significantly at about 121° C., which requires that the surfactant has a sufficient absorption capacity to the particle surface primarily due to the hydrophobic interaction. Thus, the hydrophobic structural moiety of the selected surfactant plays an important role of protecting the stability of the micron-sized suspension during the high-pressure sterilization. The hydrophobic structural moiety of the surfactant selected in the present application comprises one or more hydrocarbon chains with a total of not less than 15 carbon atoms, or the hydrophobic structural moiety of the surfactant comprises not less than 20 oxypropylene units.

In the self-sustained release immune adjuvant suspension of the present application, it is feasible to further select a combination of two or more surfactants with different hydrophilic-lipophilic balance values (HLB values) as the coating layer of the microparticles. The two surfactants with different solubility are not completely homogeneously and mutually dispersed at a microscopic level, but dispersed in a manner of local regional aggregation. Thus, once the formed coated composite particles enter the tumor, the surfactant with a higher HLB value is first dissolved and some minor openings or minor defect areas are formed on the coating layer surface of the microparticles, so that the surface area of the inner lipid soluble immune adjuvant microparticles varies gradually, and the active ingredients are gradually released. Further, a more personalized combinational scheme of medicaments (meeting the practical requirement of different patients) can be provided for doctors' selection by adjusting the selection or modulating the ratio of two or more surfactants in accordance with the practical requirement of different tumors and human bodies. And, a combination of surfactants with two or more hydrophilic-lipophilic balance values (HLB values) can further improve the stability of the microparticles during the high-pressure sterilization.

The present application further provides a novel preparation method for a self-sustained release immune adjuvant suspension because the present R&D team found that when the ball milling process was scaled up, ceramic particles were likely to be produced in the ball milling process, thereby resulting in an injection risk. Such impurities are not problematic in the preparation process of common micro- to nano-materials, but are riskier for use in human injection. To replace the current technical solution in which imiquimod is processed to microparticles by ball milling, the applicant's R&D team has performed a large number of trials-and-errors and improvements of experimental schemes, and further proposes a novel technical route of airflow pulverization in combination with high-pressure homogenization or airflow pulverization in combination with high-shear process for producing a suspension of lipid soluble immune adjuvant microparticles in micron scale. This preparation method overcomes the technical bias in the preparation process for microparticles and the practical problems during the technological improvement, that is, the high-pressure homogenization process or the high-shear process is a liquid processing method, while the lipid soluble immune adjuvant is a semi-solid agent; it is found in the experiments that if the lipid soluble immune adjuvant is directly subject to a high-pressure homogenization or a high-shear process, the homogenization valve would be blocked due to a much higher viscosity of the lipid soluble immune adjuvant than that of solutions or common solid nano-materials, so that microparticles cannot be obtained. Also, although microparticles can be partially obtained by means of direct high-shear process, the uniformity of the obtained particles are very poor, and most of the particles cannot achieve the expected effect of granulated pulverization and yield. However, in the present application, the primary powder is obtained through a preliminary airflow pulverization process, and then subject to a high-pressure homogenization or a high-shear process by adding an aqueous solution of surfactant so that the high-pressure homogenized or high-shear-treated microparticles can experience a quick surface modification. The presence of surfactant enables the lipid soluble immune adjuvant to discretely disperse in the liquid phase so that the primary powder of the lipid soluble immune adjuvant can be processed by a liquid-phase micro-nano technology to obtain a suspension of lipid soluble immune adjuvant microparticles with good dimensional uniformity.

As compared with the micro-nano particles obtained by various current technologies, the self-sustained release immune adjuvant suspension of the present application can further adapt stricter sterilization conditions, tolerate high-pressure sterilization, and still maintain the stability of the suspension and the stability of particle sizes, improving the production efficiency and safety.

By injecting the self-sustained release immune adjuvant suspension into the tumor, it can effectively enhance the immunogenic cell death induced by radiotherapy, chemotherapy or thermotherapy, and induce the anti-tumor immune response. On the one hand, the therapeutic effect produced thereby can improve the efficacy of the radiotherapy on the in-situ tumor; and on the other hand, it can obtain a stronger abscopal effect to inhibit the growth of distal tumor which is not irradiated.

To address the related technical problem, the present application further provides an imiquimod suspension formulation comprising imiquimod microparticles, a surfactant with a higher fatty acid chain, and a dispersing medium. Of those, the dispersing medium is water, normal saline or a glucose solution.

In particular, the imiquimod microparticles have an average particle size of 0.5 to 5.0 μm.

Of those, the surfactant with a higher fatty acid chain is an ionic surfactant with a higher fatty acid chain.

In particular, the surfactant with a higher fatty acid chain comprises an anionic surfactant and an amphiphilic ionic surfactant.

In particular, the surfactant with a higher fatty acid chain comprise linear alkyl carboxylates, linear alkyl sulfonates, linear alkyl sulfates, and linear alkanol sulfates, etc.

In particular, the anionic surfactant with a higher fatty acid chain is sodium oleate, sodium dodecyl sulfate, sodium stearate, sodium N-lauroyl sarcosinate, sodium cocoyl methyl taurate, sodium N-lauroyl glutamate, sodium lauryl polyoxyethylene ether carboxylate, or dodecyl phosphate.

Optionally, the surfactant with a higher fatty acid chain is a phospholipid ionic surfactant.

In particular, the phospholipid ionic surfactant is lecithin, soybean phospholipid, phosphatidylglycerol, phosphatidylethanolamine, phosphatidylserine, or phosphatidylinositol.

Optionally, the dispersing medium is water.

Optionally, the mass ratio of the surfactant with a higher fatty acid chain to imiquimod is 0.025 to 3:1.

Optionally, the mass ratio of the surfactant with a higher fatty acid chain to imiquimod is 0.1 to 1:1.

The imiquimod suspension formulation provided in the present application can be retained in the tumor for a long time and sustainedly released, and can be further combined with a therapy for eliciting the immunogenic death of tumor cells, such as chemotherapy, radiotherapy, and ethanol ablation, to significantly enhance the anti-tumor immune response. It induces a systemic anti-tumor immune response while effectively eradicating the in-situ tumor, and inhibiting the tumor metastasis and the growth of distal tumor. At the same time, the micron-sized imiquimod suspension formulation has a good stability, and can be sterilized at high temperature and high pressure to meet the safety criteria of formulation for clinic use. The micron-sized imiquimod suspension of the present application that can be terminally sterilized has characteristics of simple components, simple preparation, stable products, as well as sterility and hypopyrogen.

The present application provides a preparation method for an imiquimod suspension formulation.

It comprises the steps of:

S1: dispersing a surfactant with a higher fatty acid chain and imiquimod microparticles in a single dispersing system, and stirring to obtain a suspension;

S2: homogenizing the prepared suspension;

S3: packaging the homogenized suspension, sealing, and then sterilizing at high temperature and high pressure.

Of those, the high-temperature and high-pressure sterilization is performed at 105° C. to 145° C. for 5 to 30 min.

In particular, after high-temperature and high-pressure sterilization, the micron-sized imiquimod suspension formulation is in a state of no agglomeration or caking, or can be re-dispersed into a uniform suspension by simple shaking after caking/agglomeration.

The present application further provides use of the imiquimod suspension formulation in preparation of a formulation for antitumor therapy in combination with immunotherapy.

In particular, after mixed with a platinum-based chemotherapeutic drug, the imiquimod suspension formulation of the present application can achieve a sustained release of the chemotherapeutic drug.

In particular, after mixed with an anthracycline-based chemotherapeutic drug, the imiquimod suspension formulation of the present application can achieve a sustained release of the chemotherapeutic drug.

In particular, use of the imiquimod suspension formulation of the present application in preparation of a formulation for enhancing an anti-tumor immunotherapy is provided. In practice, an effective amount of the micron-sized imiquimod suspension formulation can be administered to a patient in need thereof, wherein the micron-sized imiquimod suspension formulation is administered by intratumoral or peritumoral injection.

Using the technical solutions of the present application, the following beneficial effects can be provided:

The micron-sized imiquimod suspension of the present application which can be terminally sterilized provides a dosage form of injectable imiquimod suspension so that the imiquimod can be used in the immunotherapy for non-superficial tumors. With the aid of the surfactant with a higher fatty acid chain, a sterile, pyrogen-free, stable dosage form can be obtained by high-temperature and high-pressure sterilization, which has a good uniformity and stability. As compared with the micromolecular injectable dosage form of imiquimod hydrochloride, this micron-sized imiquimod suspension has a longer half-life in tumors; as compared with the imiquimod nano-particle formulation, this micron-sized imiquimod suspension is more feasible to scale up, can maintain a long-term stability of the dosage form after high-temperature and high-pressure sterilization, and can meet the requirement for clinic use.

The imiquimod suspension of the present application can be used, in combination with radiotherapy, chemical ablation and other therapeutic means, in an enhanced anti-tumor immunotherapy via intertumoral or peritumoral injection. Also, when injected after premixed with a platinum- or anthracycline-based chemotherapeutic drug, it can result in the sustained release of the chemotherapeutic drug, pro-long the action period of the agent at the site of lesion, enhance the anti-tumor immune response of the combinational chemotherapeutic drug, effectively inhibit the growth of distal tumors, and prevent the tumor(s) from metastasis and recurrence.

Without being bound by any theory, the following examples are only for illustrating the self-sustained release immune adjuvant suspension, the preparation method, and the use of the present application or the like, and are not intended to limit the scope of the application of the application.

EXAMPLES

Example A: Preparation of Formulation

Example A1

FIG. 1 is a schematic view showing the preparation of a self-sustained release immune adjuvant suspension. A self-sustained release immune adjuvant suspension was prepared by reference to FIG. 1, and the preparation method was as follows:

A solid of lipid soluble immune adjuvant imiquimod R837 was subject to airflow pulverization at a pulverization pressure of 6 to 10 bar to give micron-sized imiquimod R837 powder.

To a mixture of the micron-sized immune adjuvant imiquimod R837 (preferably, 2 g of R837) and a surfactant Poloxamer 188 at a ratio of 1:(0.025 to 5) was added a proper amount of Poloxamer 188 (0.05 g, 0.3 g, 0.6 g, 1 g, 2 g, 4 g, 6 g, 8 g, or 10 g), and then 100 mL of water for injection was added. The mixture was stirred at 100 to 500 rpm for 0.5 to 2 h to give a suspension.

The resultant suspension was homogenized twice to four times at high pressure of 750-1200 bar to give a suspension, which was diluted with water for injection to an imiquimod concentration of 6.0 mg/mL. The suspension was sucked by a peristaltic pump to 10 mL ampules, with 6 ml in each ampule and total 30 ampules. After heat sealing, a micron-sized suspension was obtained and subject to moist heat sterilization at 105° C. to 150° C. for 15-20 min.

Poloxamer 188 is a novel type of polymeric non-ionic surfactant, and can be used in various application including emulsifiers, stabilizers, and stabilizers. It can be used to further enhance the water dispersibility and stability of R837.

The hydrophobic structural moiety of the surfactant as used comprises not less than 20 oxypropylene units; in particular, including Poloxamer 188, Poloxamer 237, Poloxamer 338, Poloxamer 407. Alternatively, the hydrophobic structural moiety of the surfactant comprises one or more hydrocarbon chains with not less than 15 carbon atoms; in particular, including at least one of sorbitan sesquioleate, soybean phospholipid, glyceryl monostearate, polysorbate 40, polysorbate 60, polysorbate 65, polysorbate 80, polysorbate 85, sorbitan stearate (Span 60), stearate, vitamin E polyethylene succinate, polyoxyethylene alkyl ether, polyoxyethylene stearate, polyoxyl (40) stearate, sucrose stearate, a polyoxyethylenated castor oil derivative, cetomacrogol 1000, or lecithin.

Poloxamers are a series of versatile pharmaceutical adjuvants due to their non-toxicity, non-antigenicity, non-sensitization, non-irritation, non-hemolysis, and chemical stability. Poloxamer 188 is one of the series of adjuvants with good safety. Poloxamer 188 enables the micron-sized powder obtained by the airflow pulverization of imiquimod to be processed by a liquid micro-nano technology to give an imiquimod microparticles suspension with good dimensional uniformity, and also helps to ensure the water dispersibility and stability of the imiquimod microparticle suspension (6.0 mg/mL or less) after high-pressure sterilization.

However, the imiquimod microparticle suspension coated with Poloxamer 188 can maintain a good suspension stability after sterilized at high-pressure sterilization at a low concentration (6.0 mg/mL), but too high concentration of imiquimod during sterilization would lead to agglomeration of the sterilized imiquimod incapable of stable suspension. Lecithin is a naturally-occurring surfactant, and the imiquimod microparticles which were homogenized at high pressure using lecithin as stabilizer have good stability. Even if the suspension is sterilized at high temperature and high imiquimod concentration, it would not yet agglomerate and maintain a stable suspension.

TABLE 1

| Preparation Process and Data of Imiquimod/Surfactant Suspension | | | |
|---|---|---|---|
| Method | Average Particle Size (Microns) | Maximum Particle Size (Microns) | Remarks |
| Stirring | 20 to 40 | >150 | The imiquimod active ingredient was directly added into an aqueous solution of Poloxamer 188, and stirred for 12 h. |
| Ball milling | 0.9 to 1.5 | 5 to 20 | Ceramic powder impurities were easy to introduce after process scaling up, which was not conducive to the preparation of suspension for injection |
| Airflow pulverization (Solid) | 1 to 2.5 | 8 to 18 | Airflow pulverization resulted in solids which could not be directly used and need to be further prepared to form a suspension. |
| Airflow pulverization + high-pressure homogenization | 1 to 2 | 5 to 8 | The airflow-pulverized sample was added into an aqueous solution of Poloxamer 188, and homogenized at high pressure. |
| Airflow pulverization + high shear process | 1 to 2 | 10 to 20 | The airflow-pulverized sample was added into an aqueous solution of Poloxamer 188, and treated at high shear. |

The novel technical route of airflow pulverization in combination with high-pressure homogenization or airflow pulverization in combination with high-shear process produces a suspension of lipid soluble immune adjuvant microparticles at a micron level. This preparation method overcomes the technical bias in the preparation process of microparticles and the practical problems. The high-pressure homogenization process or the high-shear process is a liquid processing method, while the lipid soluble immune adjuvant is a semi-solid agent. It is found in the experiments that if the lipid soluble immune adjuvant is directly subject to a high-pressure homogenization or a high-shear process, the homogenization valve would be blocked so that microparticles cannot be obtained. Also, although microparticles can be partially obtained by a direct high-shear method, the uniformity of the obtained particles are very poor, and most of the particles cannot achieve the expected granulation and pulverization effect and yield. However, in the present application, the primary powder is obtained by first performing an airflow pulverization process, followed by a high-pressure homogenization or a high-shear process under the solution condition of adding a surfactant solution so that the high-pressure homogenized or high-shear-treated microparticles can experience a quick surface finishing and surface modification. Due to the presence of surfactant, the lipid soluble immune adjuvant can be discretely dispersed in the liquid phase so that the primary powder of the lipid soluble immune adjuvant can be processed by a liquid micro-nano technology to obtain a suspension of lipid soluble immune adjuvant microparticles with good dimensional uniformity.

TABLE 2

| Water Dispersibility Characteristic of Imiquimod Obtained by Adding an Airflow Pulverized Imiquimod Microparticle Powder into Aqueous Solutions of Different Surfactants (With a Mass Ratio of Imiquimod:Surfactant = 1:3), Followed By Homogenizing At High Pressure. | |
|---|---|
| Added Surfactant | Water Dispersibility Of Imiquimod After Airflow Pulverization + High-Pressure Homogenization |
| No added | Macroparticles agglomeration as visually observed. |
| Poloxamer 124 (P124) | Uniformly dispersed, and a milk white suspension obtained. |
| Poloxamer 188 (P188) | Uniformly dispersed, and a milk white suspension obtained. |
| Poloxamer 407 (P407) | Uniformly dispersed, and a milk white suspension obtained. |
| Tween 80 | Uniformly dispersed, and a milk white suspension obtained. |
| Lecithin | Uniformly dispersed, and a milk white suspension obtained. |
| Polyoxyethylenated (35) castor oil | Uniformly dispersed, and a milk white suspension obtained. |
| Vitamin E polyethylene glycol succinate | Uniformly dispersed, and a milk white suspension obtained. |
| P188 & Lecithin | Uniformly dispersed, and a milk white suspension obtained. |
| PEG 800 | It has a certain dispersing effect, but there are visually visible agglomeration. |
| Sodium carboxymethylcellulose | It has a certain dispersing effect, but there are visually visible agglomeration. |

TABLE 3

Re-Dispersibility of Imiquimod Suspensions with Different Surfactants Added after High-Pressure Sterilization (a Mass Ratio of P188:Imiquimod Surface = 1:3)

| Added Surfactant | Re-Dispersibility After High-Pressure Sterilization |
|---|---|
| Poloxamer 124 | After shaking, there was still a minor amount of caking. |
| Poloxamer 188 | After shaking, it could be restored to the homogeneously dispersed milk white suspension |
| Poloxamer 407 | After shaking, it could be restored to the uniformly dispersed milk white suspension |
| Tween 80 | After shaking, it could be restored to the uniformly dispersed milk white suspension |
| Lecithin | After shaking, it could be restored to the homogeneously dispersed milk white suspension |
| Polyoxyethylenated (35) castor oil | After shaking, it could be restored to the homogeneously dispersed milk white suspension |
| Vitamin E polyethylene glycol succinate | After shaking, it could be restored to the homogeneously dispersed milk white suspension |
| P188 & Lecithin | After shaking, it could be restored to the homogeneously dispersed milk white suspension |
| PEG 800 | Bulky agglomeration occurred and could not be re-dispersed. |
| Sodium carboxymethyl-cellulose | Bulky agglomeration occurred and could not be re-dispersed. |

Since the microparticle suspension need to undergo standard high-pressure sterilization operation to meet the sterile requirement prior to injection into the tumor, it is necessary to ensure that the microparticles would not agglomerate significantly under the condition of about 121° C. Thus, it is required that the surfactant has a sufficient absorption capacity to the particle surface that is primarily due to the hydrophobic interaction, and hence the hydrophobic structural moiety of the selected surfactant is of importance for protecting the stability of the micron-sized suspension under the high-pressure sterilization. The hydrophobic structural moiety of the surfactant selected in the present application comprises one or more hydrocarbon chains with a total of not less than 15 carbon atoms, or the hydrophobic structural moiety of the surfactant comprises not less than 20 oxypropylene units. As shown in Tables 2 and 3, Poloxamer P124 is unstable after sterilization at high pressure sterilization due to insufficient hydrophobic structural moiety

TABLE 4

Suspension Stability of Imiquimod Suspension Dispersed by Addition of P188 at Different Ratios (the Concentration of R837 = 6.0 mg/mL During Sterilization) after Sterilization High Pressure.

| Poloxamer 188:R837 | Suspension Stability After High-Pressure Sterilization |
|---|---|
| 0.5:1 | A great number of particulate aggregates |
| 1:1 | A minor number of particulate aggregates |
| 2:1 | A minor number of particulate aggregates |
| 3:1 | Uniformly dispersed and no particulate aggregate |
| 5:1 | Uniformly dispersed and no particulate aggregate |

Although in theory, the more the dispersant, the better the dispersibility, the ratio is not typically greater than 5:1 because Poloxamer 188 (P188) itself is viscous, too high concentration will lead to high viscosity. In addition, the introduction of impurities caused by too much dispersant should be avoided.

TABLE 5

Suspension Stability of Imiquimod Suspensions Dispersed with P188 Having Different Concentrations after High-Pressure Sterilization (a Mass Ratio of P188:Imiquimod R837 = 3:1). The P188-Coated Imiquimod Suspension Can Maintain Good Stability after High-Pressure Sterilization at Low R837 Concentration, but Has Remarkably Decreased Stability after High-Pressure Sterilization at High R837 Concentration.

| Concentration Of R837 During Sterilization | Suspension Stability after High-Pressure Sterilization |
|---|---|
| 3.0 mg/mL | Uniformly dispersed and no particulate aggregate |
| 6.0 mg/mL | Uniformly dispersed and no particulate aggregate |
| 9.0 mg/mL | Some particulate aggregates |
| 12.0 mg/mL | A great number of particulate aggregates |
| 15.0 mg/mL | A great number of particulate aggregates |
| 18.0 mg/mL | A great number of particulate aggregates |

TABLE 6

Suspension Stability of Imiquimod Suspension Dispersed by Addition of Lecithin at Different Ratios (The Concentration Of R837 = 6.0 mg/mL Or 18 mg/mL During Sterilization) after High-Pressure Sterilization Lecithin Enables a Suspension with High Concentration of Imiquimod to Maintain Good Suspension Stability After Sterilization at High Pressure Even at a Low Ratio

| Lecithin:R837 | Concentration Of R837 During Sterilization | Suspension Stability After High-Pressure Sterilization |
|---|---|---|
| 0.025:1 | 6.0 mg/mL | Uniformly dispersed and no particulate aggregate |
| 0.05:1 | 6.0 mg/mL | Uniformly dispersed and no particulate aggregate |
| 0.1:1 | 6.0 mg/mL | Uniformly dispersed and no particulate aggregate |
| 0.25:1 | 6.0 mg/mL | Uniformly dispersed and no particulate aggregate |
| 0.5:1 | 6.0 mg/mL | Uniformly dispersed and no particulate aggregate |
| 1:1 | 6.0 mg/mL | Uniformly dispersed and no particulate aggregate |
| 0.025:1 | 18.0 mg/mL | Uniformly dispersed and no particulate aggregate |
| 0.05:1 | 18.0 mg/mL | Uniformly dispersed and no particulate aggregate |
| 0.1:1 | 18.0 mg/mL | Uniformly dispersed and no particulate aggregate |
| 0.25:1 | 18.0 mg/mL | Uniformly dispersed and no particulate aggregate |
| 0.5:1 | 18.0 mg/mL | Uniformly dispersed and no particulate aggregate |
| 1:1 | 18.0 mg/mL | Uniformly dispersed and no particulate aggregate |

Example A2

A solid of lipid soluble immune adjuvant resiquimod (R848) was subject to airflow pulverization at a pulverization air pressure of 6 to 10 bar to give micron-sized resiquimod (R837).

To a mixture of the micron-sized immune adjuvant resiquimod (R848) (preferably, 2 g of R837) and a surfactant Poloxamer 407 at a ratio of 1:(0.025 to 5) was added a proper amount of Poloxamer 407 (0.005 g, 2 g, 0.2 g, 0.4 g, 0.8 g, or 1 g), and then 100 mL of water for injection was added. The mixture was stirred at 100 to 500 rpm for 0.5 to 2 h to give a suspension.

The suspension was subject to high-pressure homogenization twice to four times at 750-1200 bar to give a suspension, which was sucked by a peristaltic pump into 10 mL ampules, with 6 mL in each ampule and a total of 30 ampules. After heat sealing, a micron-sized suspension was obtained, which was subject to moist heat sterilization at 105° C. to 150° C. for 15-20 min.

Poloxamer 407 is a novel type of polymeric non-ionic surfactant, which can be used in various applications including emulsifiers, stabilizers, and solubilizers for further enhancing the water dispersibility and stability of R848.

Example A3

An amount of lipid soluble immune adjuvant glucopyranoside lipid A (MPLA) was taken; and a mixture of Poloxamer 188 and lecithin at a mass ratio of 9:1 was selected as the surfactant. The other steps of the preparation method were the same as those of Example A2.

Example A4

The other steps of the preparation method were the same as those of Example A1, except that an amount of lipid soluble immune adjuvant imiquimod (R837) was taken; and a mixture of Poloxamer 188 and lecithin at a mass ratio of 3:1 was selected as the surfactant. The dosing concentrations of different surfactants produce some effects on the suspension stability of R837 after high-pressure sterilization, and the results are shown in Table 7. In the presence of lecithin, the long-term stability of R837 after high-pressure sterilization is better than that of R837 solubilized with P188 alone, and the resultant particles have a smaller particle size and a better uniformity. And the effect of the dosing concentration can be proportionally scaled up, thereby achieving the technical effect of increasing the final concentration of R837.

TABLE 7

Suspension Stability after High-Pressure Sterilization of R837 Incorporating Different Concentrations of Surfactants

| R837:Poloxamer 188:Lecithin | Long-Term Stability After High-Pressure Sterilization |
|---|---|
| 12 mg/mL:36 mg/mL:0 mg/mL | A great number of particulate aggregates appeared |
| 12 mg/mL:36 mg/mL:12 mg/mL | Uniformly dispersed and no particulate aggregate appeared |
| 18 mg/mL:54 mg/mL:0 mg/mL | A great number of particulate aggregates appear. |
| 18 mg/mL:54 mg/mL:18 mg/mL | Uniformly dispersed and no particulate aggregate |

It can be seen that mixing two surfactants can further improve the suspension stability of the self-sustained release immune adjuvant suspension during the high-pressure sterilization, especially at higher surfactant concentration it is outstanding. A combination of two or more surfactants with different hydrophilic-lipophilic balance values (HLB values) or two surfactants with different hydrophilic structural moieties (e.g., one surfactant containing not less than 20 oxypropylene units, or one surfactant containing one or more hydrocarbon chains containing a total of not less than 15 carbon atoms) were used as the coating layer of microparticles. Two surfactants with different solubility were not completely homogeneously and mutually dispersed, but formed a relatively homogeneous and locally aggregated dispersion structure. Once the formed coated composite particles entered the tumor, the surfactant with a higher HLB value was first dissolved and some minor openings or minor defect areas were formed on the coating layer surface of the microparticles, so that the surface area of the inner fat-soluble immune adjuvant microparticles varied gradually, and the active ingredients were gradually released. Further, a plurality of pharmaceutical combination schemes can be obtained by adjusting the selection or ratio of the two or more surfactants in accordance with the practical requirement of different tumors and human bodies.

TABLE 8

Change in Particle Size of R837 with Different Ratios of Surfactants Added After High-Pressure Sterilization

| R837:Poloxamer 188:Lecithin | Processing Phase | D50 (MM) | D90 (MM) | Dmax (MM) |
|---|---|---|---|---|
| 18 mg/mL:0:18 mg/mL | Before sterilization | 1.273 | 2.641 | 5.408 |
| 18 mg/mL:0:18 mg/mL | After sterilization | 4.470 | 12.077 | 30.581 |
| 18 mg/mL:18 mg/mL:18 mg/mL | Before sterilization | 1.339 | 2.737 | 5.452 |
| 18 mg/mL:18 mg/mL:18 mg/mL | After sterilization | 2.933 | 7.474 | 16.901 |

At the same time, it is shown in Table 8 that the R837 obtained in the presence of both lecithin and P188 has a minimum change in particle size before and after sterilization and a smaller distribution range of particle size, namely, the co-existence of lecithin and P188 is more conductive to the stability of the sample during sterilization. Of those, D50 is the corresponding particle size when the cumulative particle size distribution in the sample reaches 50%, D90 is the corresponding particle size when the cumulative particle size distribution in the sample reaches 90%, and $D_{max}$ is the maximum particle size of the particles in the sample. The smaller the difference among the three parameters, the higher the uniformity of the sample particles. In the experiment, it is also observed that the suspension samples with both in which P188 and lecithin would not adhere onto the wall after long-term storage. It is worthing to indicate that the size uniformity of microparticles is an important parameter to ensure that the drug has a stable and repeatable release behavior in vivo.

Example A5

Preparation of the First Composition:

A solid of lipid soluble immune adjuvant imiquimod R837 was subject to airflow pulverization at a pulverization pressure of 6 to 10 bar to give micron-sized imiquimod R837 powder.

To a mixture of the micron-sized immune adjuvant imiquimod R837 (preferably, 2 g of R837) and a surfactant Poloxamer 188 at a ratio of 1:(0.025 to 5) was added a proper amount of Poloxamer 188 (0.05 g, 0.3 g, 0.6 g, 1 g, 2 g, 4 g, 6 g, 8 g, or 10 g), and then 100 mL of water for injection was added. The mixture was stirred at 100 to 500 rpm for 0.5 to 2 h to give a suspension.

The resultant suspension was homogenized twice to four times at high pressure of 750-1200 bar to give a suspension, and diluted with water for injection to an imiquimod concentration of 6.0 mg/mL. The suspension was sucked by a peristaltic pump to a 10 mL ampule, with 6 ml in each ampule and total 30 ampules. After heat sealing, a micron-sized suspension was obtained and subject to moist heat sterilization at 105° C. to 150° C. for 15-20 min.

Preparation of the Second Composition:

A solution of sodium alginate/mannitol or sodium alginate/lactose was formulated at a ratio of 1:(1-5), wherein the sodium alginate solution has a concentration of 10 mg/mL, 20 mg/mL, or 40 mg/mL, the mannitol or lactose had a final concentration of 1-50 mg/mL, 20-100 mg/mL, or 40-200 mg/mL; the sodium alginate solution was stirred homogeneously, and then mannitol or lactose was added; and the mixture was packaged into penicillin bottles, pre-cooled, lyophilized, filled with nitrogen, and sealed.

Prior to the experiment, two compositions were intensively mixed, placed in a dialysis bag (with a permeable molecular weight of 12000-14000 Da), and then dialyzed in buffer solutions at different pHs. In the control group, an imiquimod suspension was directly placed in a dialysis bag (with a permeable molecular weight of 12000-14000 Da), dialyzed in buffer solutions with different pHs, and then monitored for the release of Imiquimod. Of those, the buffer solution at pH7.4 is a phosphate buffer with 2 mM $CaCl_2$) added, and the buffering solution at pH4.0 is an acetic acid/sodium acetate buffer solution.

The change in the release ratio of imiquimod from the sodium alginate/calcium ionic hydrogel (ALG) with time is shown in Table 9. imiquimod can be more rapidly released under acid condition. Moreover, under both the pH conditions, the presence of sodium alginate/calcium ionic gel can significantly decrease the release rate of Imiquimod, achieving the sustained release effect.

TABLE 9

Release Data of Imiquimod from Sodium Alginate/Calcium Ion Hydrogel

| pH conditions | Composition | 5 min | 1 h | 3 h | 6 h | 12 h | 24 h |
|---|---|---|---|---|---|---|---|
| pH 7.4 | R837 | 2.3% | 4.8% | 7.3% | 12.9% | 14.0% | 17.2% |
| | R837 + ALG | 0.0% | 1.3% | 2.7% | 3.4% | 4.2% | 5.6% |
| pH 4.0 | R837 | 5.7% | 42% | 75% | 89% | 94% | 98% |
| | R837 + ALG | 1.2% | 12.3% | 27.6% | 50.1% | 71.0% | 85.4% |

Example B. Investigation of Co-Suspending Agent

Example B1: Preparation of Imiquimod Suspension

Imiquimod suspension formulations were prepared with various suspending agents.

An imiquimod suspension was prepared by taking the surfactant with a higher fatty acid chain lecithin as example.

S1: Formulating lecithin into homogeneous suspensions with different concentrations, adding imiquimod powder to an imiquimod concentration of 1 to 18 mg/mL, and stirring the suspension;

S2: homogenizing the suspension obtained in the step S1;

S3: packaging the homogenized suspension, capping, and sterilizing at high temperature and high pressure The sterilizing at high temperature and high pressure was performed at 110° C. to 145° C. for 10-30 min.

Example B2: Effect of Different Suspending Agents on the Stability of Imiquimod Suspension The selection of suspending agents should be based on several factors. First, as a suspending agent for injectable dosage form, it is preferable to select an approved injection-grade pharmaceutical adjuvant to avoid any safety hazard from the suspending agent itself; and secondly, the suspending agent itself cannot react with drug molecules to change the drug activity or increase the drug toxicity.

It is mainly judged in three aspects whether a suspending agent is conducive to the stability of the imiquimod suspension after terminal sterilization.

First, the sample was observed for change in suspension appearance before and after high-pressure sterilization, and defined as stable, average, and unstable in accordance with the appearance change. In particular, it is observed for the presence of cases such as visually visible particle or caking, wall adherence, and disability of re-suspension, and recorded accordingly. If a sample does not present the above phenomenon, it is deemed to be stable after sterilization; if a sample presents the above phenomenon after sterilization but re-disperse to give a uniform suspension by shaking or vibrating, it is deemed to be average after sterilization; and if a sample presents the above phenomenon after sterilization and fail to re-disperse to give any uniform suspension after varying degrees of shaking or vibrating, it is deemed to be unstable.

Second, the imiquimod suspension formulation was detected for the particle size distribution before and after the step D3 of Example B1 by means of dynamic light scattering. Key parameters in the detection are D50, D90. Of those, D50 is a median particle size of the particles in the suspension, meaning that 50% of the particles in the suspension have a particle size below this value, which is a classic value indicating the particle size and often used to indicate an average particle size of particles; and D90 means that 90% of the particles in the system have a particle size below this value. The difference between D50 and D90 can explain the span of particle size distribution and the uniformity of particle size. During the analysis of test data, we mainly judge the values of D50 and D90 and the changes in D50 and D90 before and after sterilization. The larger the values of D50 and D90, the worse the particle dispersibility; and the greater the increases of D50 and D90, the worse the stability of the sample. Therefore, both larger values of D50 and D90 and larger increase of the two values suggest that the suspending agent used in the sample is not effective for suspension to obtain a formulation product that can be subject to moist heat sterilization.

Third, the sterilized sample was stored for a long time and observed for the sample status and the average particle size of the tested samples. If the sample can be re-suspended and D50 and D90 do not rise significantly or the difference between D50 and D90 is relatively small, it can be deemed conducive to improve the stability of the micron-sized imiquimod suspension. Herein, the condition of long-term storage is 2-8° C. for 12 months.

Figure 2:
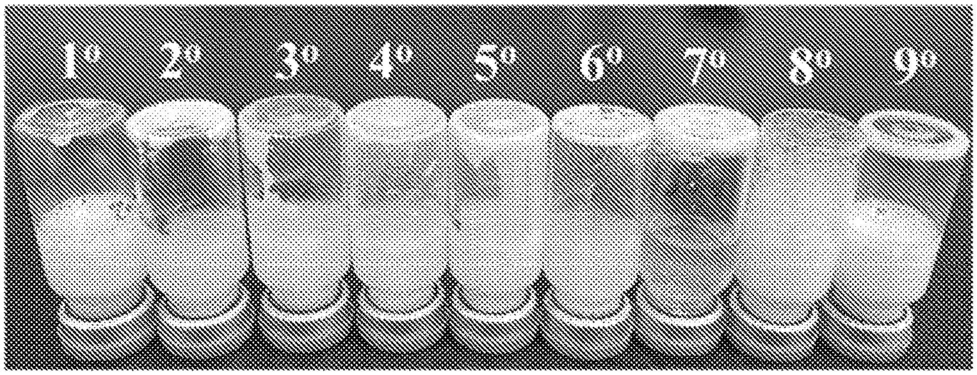
FIG. 2 is a photograph showing micron-sized imiquimod suspensions incorporating different surfactants with a higher fatty acid chain, which had underwent shaking after sterilization.

Based on the above two criteria, the particle size values and phenomena of different samples before and after sterilization and after long-term storage were recorded as shown in Table 1, and the statuses of different samples were recorded by photographs as shown in FIG. 2.

In FIG. 2, the different types of surfactants added into Samples 1 to 9 were: lecithin, Tween-80, Tween-20, Poloxamer 188, Poloxamer 407, polyoxyethylenated castor oil, vitamin E polyethylene glycol succinate, sodium oleate, phosphatidyl glycerol.

In FIG. 2, Samples 1, 8, and 9 are homogeneously dispersed suspensions, and the rest of the samples showed different degrees of wall adhesion, caking, or even precipitation.

TABLE 10

Record chart of change in particle size and phenomena of imiquimod suspensions with different types of suspending agents added before and after sterilization and long-term storage after sterilization (wherein, "after sterilization" is within 1 weeks after the sterilization, and "long-term storage" refers to storage for 12 months).

| Surfactant with Higher Fatty Acid Chain Type | Surfactant with Higher Fatty Acid Chain Name | Mass Ratio (Surfactant with a higher fatty acid chain: R837) | Time Point of Detection | D50 (μm) | D90 (μm) | Stability |
|---|---|---|---|---|---|---|
| Zwitterionic surfactant | Lecithin | 0.25:1 | Before sterilization | 1.14 | 2.35 | Good |
| | | | After sterilization | 1.99 | 4.79 | Good |
| | | | long-term storage | 2.51 | 5.06 | Good |
| | | 1:1 | Before sterilization | 1.12 | 2.55 | Good |
| | | | After sterilization | 1.93 | 5.84 | Good |
| | | | long-term storage | 2.01 | 5.98 | Good |
| | | 3:1 | Before sterilization | 1.18 | 4.91 | Good |
| | | | After sterilization | 1.88 | 7.05 | Good |
| | | | long-term storage | 1.73 | 5.53 | Good |
| Nonionic surfactant | Tween-80 | 0.25:1 | Before sterilization | 1.08 | 2.18 | Good |
| | | | After sterilization | 4.20 | 12.54 | Unstable |
| | | | long-term storage | 5.89 | 13.87 | Unstable |
| | | 1:1 | Before sterilization | 1.10 | 2.26 | Good |
| | | | After sterilization | 4.55 | 12.39 | Unstable |
| | | | long-term storage | 8.95 | 40.21 | Unstable |

TABLE 10-continued

Record chart of change in particle size and phenomena of imiquimod suspensions with different types of suspending agents added before and after sterilization and long-term storage after sterilization (wherein, "after sterilization" is within 1 weeks after the sterilization, and "long-term storage" refers to storage for 12 months).

| Surfactant with Higher Fatty Acid Chain Type | Surfactant with Higher Fatty Acid Chain Name | Mass Ratio (Surfactant with a higher fatty acid chain: R837) | Time Point of Detection | D50 (μm) | D90 (μm) | Stability |
|---|---|---|---|---|---|---|
| | | 3:1 | Before sterilization | 1.17 | 2.47 | Good |
| | | | After sterilization | 6.45 | 35.35 | Unstable |
| | | | long-term storage | 6.22 | 43.91 | Unstable |
| Nonionic surfactant | Tween-20 | 0.25:1 | Before sterilization | 0.95 | 1.85 | Good |
| | | | After sterilization | 3.79 | 8.04 | Unstable |
| | | | long-term storage | 6.55 | 12.75 | Unstable |
| | | 1:1 | Before sterilization | 0.98 | 1.91 | Good |
| | | | After sterilization | 3.56 | 14.12 | Unstable |
| | | | long-term storage | 8.64 | 25.46 | Unstable |
| | | 3:1 | Before sterilization | 1.08 | 2.05 | Good |
| | | | After sterilization | 8.56 | 55.32 | Unstable |
| | | | long-term storage | 11.00 | 88.87 | Unstable |
| Nonionic surfactant | Poloxamer 188 | 0.25:1 | Before sterilization | 2.59 | 5.49 | Good |
| | | | After sterilization | 7.57 | 16.14 | Average |
| | | | long-term storage | 11.49 | 31.60 | Unstable |
| | | 1:1 | Before sterilization | 2.02 | 4.30 | Good |
| | | | After sterilization | 5.24 | 11.35 | Average |
| | | | long-term storage | 9.58 | 18.63 | Unstable |

TABLE 10-continued

Record chart of change in particle size and phenomena of imiquimod suspensions with different types of suspending agents added before and after sterilization and long-term storage after sterilization (wherein, "after sterilization" is within 1 weeks after the sterilization, and "long-term storage" refers to storage for 12 months).

| Surfactant with Higher Fatty Acid Chain Type | Surfactant with Higher Fatty Acid Chain Name | Mass Ratio (Surfactant with a higher fatty acid chain: R837) | Time Point of Detection | D50 (μm) | D90 (μm) | Stability |
|---|---|---|---|---|---|---|
| | | 3:1 | Before sterilization | 1.43 | 3.01 | Good |
| | | | After sterilization | 2.75 | 7.19 | Unstable |
| | | | long-term storage | 9.09 | 20.25 | Unstable |
| Non-ionic surfactant | Poloxamer 407 | 0.25:1 | Before sterilization | 0.98 | 1.92 | Good |
| | | | After sterilization | 2.29 | 5.44 | Average |
| | | | long-term storage | 5.08 | 10.44 | Unstable |
| | | 1:1 | Before sterilization | 1.05 | 2.16 | Good |
| | | | After sterilization | 3.07 | 9.11 | Average |
| | | | long-term storage | 5.07 | 10.92 | Unstable |
| | | 3:1 | Before sterilization | 1.18 | 2.49 | Good |
| | | | After sterilization | 4.75 | 16.45 | Average |
| | | | long-term storage | 5.56 | 14.87 | Unstable |
| Non-ionic surfactant | Polyoxyethylenated castor oil | 0.25:1 | Before sterilization | 1.05 | 2.17 | Good |
| | | | After sterilization | 2.67 | 9.22 | Unstable |
| | | | long-term storage | 14.33 | 10.74 | Unstable |
| | | 1:1 | Before sterilization | 1.17 | 2.52 | Good |
| | | | After sterilization | 5.26 | 19.71 | Unstable |
| | | | long-term storage | 10.74 | 24.80 | Unstable |
| | | 3:1 | Before sterilization | 1.10 | 2.27 | Good |

TABLE 10-continued

Record chart of change in particle size and phenomena of imiquimod suspensions with different types of suspending agents added before and after sterilization and long-term storage after sterilization (wherein, "after sterilization" is within 1 weeks after the sterilization, and "long-term storage" refers to storage for 12 months).

| Surfactant with Higher Fatty Acid Chain Type | Surfactant with Higher Fatty Acid Chain Name | Mass Ratio (Surfactant with a higher fatty acid chain: R837) | Time Point of Detection | D50 (μm) | D90 (μm) | Stability |
|---|---|---|---|---|---|---|
| | | | After sterilization | 4.26 | 10.07 | Unstable |
| | | | Long-term storage | 13.99 | 19.16 | Unstable |
| Non-ionic surfactant | Vitamin E polyethylene glycol succinate | 0.25:1 | Before sterilization | 1.15 | 2.42 | Good |
| | | | After sterilization | 1.48 | 3.20 | Unstable |
| | | | Long-term storage | 1.64 | 4.03 | Unstable |
| | | 1:1 | Before sterilization | 1.05 | 2.16 | Good |
| | | | After sterilization | 22.37 | 92.38 | Unstable |
| | | | Long-term storage | 23.88 | 120.86 | Unstable |
| | | 3:1 | Before sterilization | 1.09 | 2.27 | Good |
| | | | After sterilization | 15.82 | 76.16 | Unstable |
| | | | Long-term storage | 15.45 | 113.01 | Unstable |
| Anionic surfactant | Sodium oleate | 0.25:1 | Before sterilization | 1.12 | 2.32 | Good |
| | | | After sterilization | 1.35 | 2.61 | Good |
| | | | Long-term storage | 1.37 | 2.85 | Good |
| | | 1:1 | Before sterilization | 1.14 | 2.48 | Good |
| | | | After sterilization | 1.78 | 3.76 | Good |
| | | | Long-term storage | 1.67 | 3.56 | Good |
| | | 3:1 | Before sterilization | 1.19 | 2.77 | Good |
| | | | After sterilization | 1.86 | 4.40 | Good |
| | | | Long-term storage | 1.58 | 3.50 | Good |

TABLE 10-continued

Record chart of change in particle size and phenomena of imiquimod suspensions with different types of suspending agents added before and after sterilization and long-term storage after sterilization (wherein, "after sterilization" is within 1 weeks after the sterilization, and "long-term storage" refers to storage for 12 months).

| Surfactant with Higher Fatty Acid Chain Type | Surfactant with Higher Fatty Acid Chain Name | Mass Ratio (Surfactant with a higher fatty acid chain: R837) | Time Point of Detection | D50 (μm) | D90 (μm) | Stability |
|---|---|---|---|---|---|---|
| Anionic surfactant | | 0.25:1 | Before sterilization | 1.82 | 6.22 | Good |
| | | | After sterilization | 2.12 | 11.53 | Good |
| | | | Long-term storage | 2.11 | 12.06 | Good |
| | | 1:1 | Before sterilization | 1.40 | 3.63 | Good |
| | Phosphatidyl glycerol | | After sterilization | 1.44 | 4.57 | Good |
| | | | Long-term storage | 1.52 | 4.85 | Good |
| | | 3:1 | Before sterilization | 1.35 | 3.56 | Good |
| | | | After sterilization | 1.46 | 11.49 | Good |
| | | | Long-term storage | 1.60 | 11.89 | Good |

Nine types of surfactant were selected, wherein polyoxyethylene nonionic surfactants, such as Tween-80 and Tween-20, polyoxyethylenated castor oil, or the like, would show clouding phenomenon when the solution temperature was elevated to a certain degree, that is, the interaction between the surfactant and water was destroyed by high temperature, and the solution became unstable, and when the system temperature dropped below the cloud point, some solutions would become transparent again, but some would not. Similarly, Poloxamer as polyoxyethylene surfactant is generally considered to have good water solubility, and will not show a cloud point when heated at normal pressure. However, it was found in the experiments that when Poloxamer 188 or Poloxamer 407 was used as surfactant to perform high-pressure sterilization, the short-term stability was average, the long-term stability was not easily to control, which would not achieve an expected stabilization effect. On the whole, none of the nonionic surfactants can achieve an expected effect of stabilizing the suspension, namely, they cannot help the sterilized suspension to disperse homogeneously.

In comparison with the nonionic surfactants, ionic surfactants, including anionic surfactants and zwitterionic surfactants, as suspending agents added in to the system, can ensure the long-term stability of the imiquimod suspension after sterilization. By further analyzing the structure of the suspending agents capable of stabilizing the suspension, it was found that these ionic surfactants all comprise higher fatty chain structure, and the hydrophobic moiety has a much greater molecular weight than that of the hydrophilic moiety. Thus, the use of such ionic surfactants with a higher fatty chain can effectively help the micron-sized imiquimod suspension to maintain the stability after terminal sterilization.

Example B3: Stabilization Effect of Surfactants with Other Ratios on Imiquimod In general, at the premise of ensuring the druggability, the less the inert ingredients in the pharmaceutical formulation, the less the safety risk for use and storage. Therefore, taking lecithin as example, we tried to use a lower proportion of surfactant with a higher fatty acid chain to verify the suspending effect. Suspensions with different mass ratios of lecithin to R837 microparticles were prepared by the method of Example B1, wherein the concentration of R837 was 15 mg/mL. After high-temperature and high-pressure sterilization, the suspension was detected for the particle size of microparticles, and observed for the stability. The records are shown in Table 11.

TABLE 11

Evaluation For Suspending Effect Of Low-Proportion Lecithin On R837 Suspension

| Mass Ratio (Lecithin:R837) | D90 (MM) | D50 (MM) | Stability |
|---|---|---|---|
| 0.025:1 | 1.47 | 3.16 | Good |
| 0.05:1 | 2.07 | 4.89 | Good |
| 0.1:1 | 2.01 | 4.82 | Good |
| 0.25:1 | 1.96 | 4.34 | Good |
| 0.5:1 | 1.74 | 4.26 | Good |

It can be seen from the results that the low-portion lecithin can still ensure the stability of suspension after high-temperature and high-pressure sterilization, and the particle size of the imiquimod microparticles has not change much, even as compared with samples to which a higher-portion ionic surfactant was added, it has more concentrated particle size distribution, i.e., the particle size thereof is more homogeneous. Thus, the mass ratio of the surfactant with a higher fatty acid chain to the imiquimod microparticles can be 0.025 to 3:1. In a further embodiment, the mass ratio of the phospholipid ionic surfactant to imiquimod can be 0.025-1:1.

Example B4: Studies on Types of Dispersing Medium for Imiquimod Suspension Formulation In clinic, when a large volume of injection is administered, an isotonic regulator is typically incorporated to avoid local tissue damage or micro-environment disorder caused by osmotic pressure change. Therefore, the effect of common isotonic regulator on the sterilization stability of imiquimod suspension formulation was investigated.

The imiquimod suspension formulation with a concentration of 1 mg/mL was prepared by the method of Example B1, except that the solution was prepared with normal saline or 5% dextrose solution in the step 51, and mixed with the imiquimod microparticles for homogenization. The appearance of the suspension formulation before and after high pressure sterilization, and no caking was observed, indicating that normal saline or 5% dextrose solution could be directly used as the dispersing medium of the formulation.

Further, the manufacture was scaled up, and the formulation was investigated for the product stability. After moist-heat sterilization, no caking appeared, and the product could still be dispersed well after long-term sterilization, and presents low change in particle size, further indicating the availability of the aforesaid conditions.

Example C. Comparison of Microparticles by Animal Experiment

Example C1

The in-vivo distribution behavior of the imiquimod formulation described in this example is as follows:

Experimental method: Mice were transplanted with mouse colon cancer (CT26) tumor on their backs, and randomly divided to 3 groups with 3 mice in each group for the study of drug distribution behavior.

Group 1: The mice were intratumorally injected with the micromolecule imiquimod hydrochloride with an injection dose of 6 mg/kg;

Group 2: The mice were intratumorally injected with imiquimod nano-particles (with average particle size of about 100 nm) encapsulated with polylactic-glycolic acid copolymer (PLGA) with an injection dose of 6 mg/kg; and Group 3: The mice were intratumorally injected with imiquimod microparticles (the present formulation) with an injection dose of 6 mg/kg. The mice were sacrificed at 72 h after injection, and the main organs and tumors were dissected to detect the drug level in these organs and tumor tissues.

Figure 3:
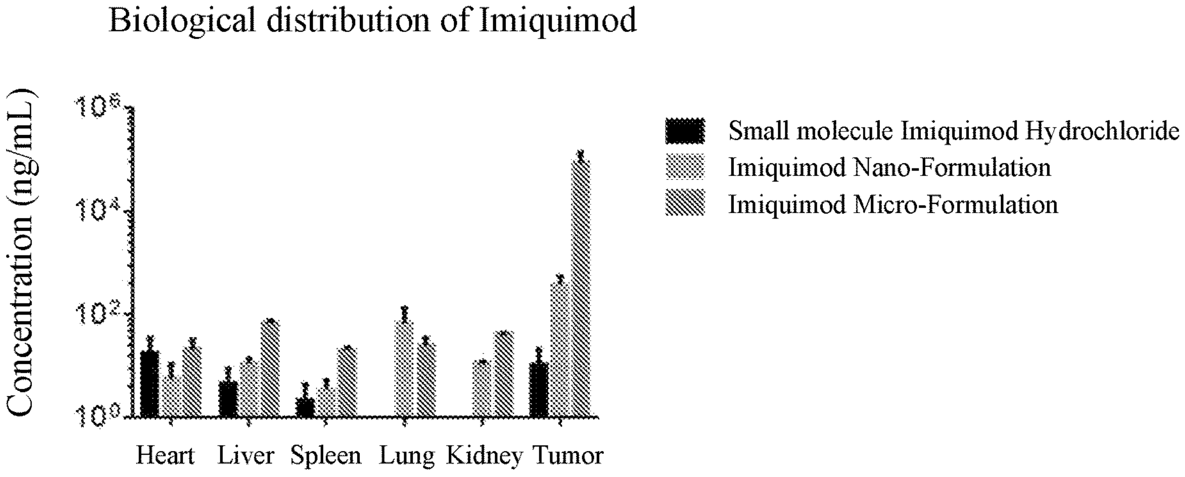
FIG. 3 is a comparison diagram showing the intratumoral retention with time after injection of self-sustained release immune adjuvant suspensions with different morphologies into a tumor.

Experiment Results: It can be seen from the graph showing the level of imiquimod in the main organs and tumor tissues of the mice (FIG. 3) that neither the micromolecule imiquimod hydrochloride nor the imiquimod/PLGA nano-formulation can ensure that most of them can remain in the tumor site, wherein the micromolecule imiquimod hydrochloride has an extremely low overall retention 72 h after intratumoral injection, while the imiquimod nano-formulation remains in other organs more. As compared with the micromolecule imiquimod hydrochloride and the imiquimod nano-formulation, the imiquimod micro-formulation of the present application has a substantially improved retention in the tumor tissues, and the imiquimod micro-formulation has the longest retention time in the tumors. It indicates that the intratumoral injection of the imiquimod micro-formulation is more favorable to the subsequent treatment.

Cancer therapy is a highly complicated comprehensive procedure because whether the immune system of an organism, or the growth mechanism of cancer cells are very complicated. Besides the explanation in other parts of the present application, the excellent therapeutic effect of this experiment may also be due to a reason of using Imiquimod-R837 micron particles. Water-insoluble R837 powder was prepared into microparticles with a particle size of 1-3 microns, which were intratumorally injected and then monitored for the pharmacokinetics and intratumoral retention time. The results are shown in Table 12, indicating that the microparticles can significantly prolong the retention time and half-life in blood circulation of imiquimod in the tumor sites to achieve a sustained release effect, thereby stimulating the immune system for a long time.

TABLE 12

Comparison Data of Retention Time of Different imiquimod Dosage Forms

| Group | | Half-Life (h) | Average Retention Time (h) |
|---|---|---|---|
| Micromolecule imiquimod hydrochloride | Average | 12 | 11 |
| | Standard Deviation | 7.3 | 5.0 |
| | Number of Samples | 3 | 3 |
| Imiquimod nano-formulation | Average | 24 | 19 |
| | Standard Deviation | 6.6 | 2.9 |
| | Number of Samples | 3 | 3 |
| Imiquimod micro-formulation | Average | 41 | 29 |
| | Standard Deviation | 5.9 | 1.3 |
| | Number of Samples | 3 | 3 |

Example C2

The in-vivo pharmacokinetics of the imiquimod formulation described in this example were as follows:

Experimental method: Mice were transplanted with mouse colon cancer (CT26) tumor on their backs, and randomly divided to 3 groups with 3 mice in each group for the pharmacokinetic study.

Group 1: The mice were intratumorally injected with micromolecule imiquimod hydrochloride with an injection dose of 6 mg/kg. Venous blood samples were collected at 5 h, 6 h, 12 h, 24 h, 48 h, 72 h after injection, and subject to a uniform measurement of imiquimod concentration to detect the imiquimod concentration in blood.

Group 2: The mice were intratumorally injected with imiquimod/PLGA nano-particles (with an average particle size of about 100 nm) with an injection dose of 6 mg/kg. Venous blood samples were collected at 5 h, 6 h, 12 h, 24 h, 48 h, 72 h after injection, and subject to a uniform measurement of imiquimod concentration to detect the imiquimod concentration in blood.

Group 3: The mice were intratumorally injected with imiquimod microparticles (the present formulation) with an injection dose of 6 mg/kg. Venous blood samples were collected at 5 h, 6 h, 12 h, 24 h, 48 h, 72 h after injection, and subject to a uniform measurement of imiquimod concentration to detect the imiquimod concentration in blood.

Figure 4:
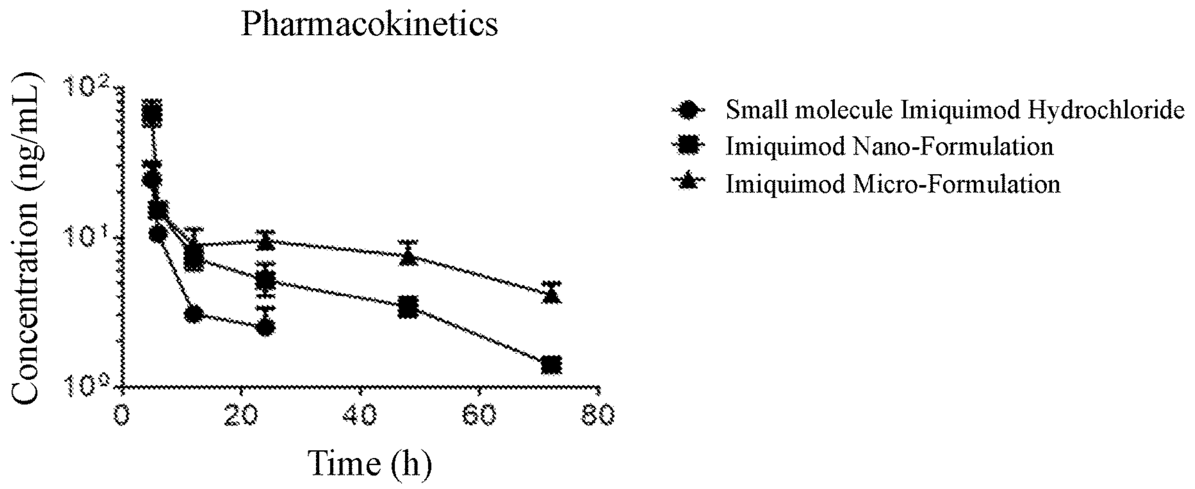
FIG. 4 is a comparison diagram showing the blood concentration over time after injection of self-sustained release immune adjuvant suspensions with different morphologies into a tumor.

Experiment Results: It can be seen from the curve of blood concentration of drug with time (FIG. 4) and the statistical analysis table of blood circulation (Table) that the micromolecule imiquimod hydrochloride is quickly cleared, and the blood concentrations of drug thereof at 48 h and 72 h have been below the limit of detection. As compared with the imiquimod nano-formulation, the micro-formulation has longer half-life in blood circulation and longer average retention time of drug.

Example C3

The particular effect of this example on the improvement of radiotherapy is as follows:

Experimental method: Mice were transplanted with mouse colon tumor on the left and the right sides of the back in mice (one on the right side was deemed an in-situ tumor, and the other on the left side was deemed a distal tumor). The tumor-bearing mice were divided into 6 groups with 6 mice in each group for the therapeutic experiments of radiotherapy in combination with immunotherapy.

Group 1: The tumor in mice was not subject to any treatment, whether by drug injection or radiotherapy;

Group 2: The in-situ tumor in mice was subject to radiotherapy alone, once per day for 5 consecutive days, and the distal tumor was not subject to any treatment;

Group 3: The in-situ tumor was subject to intratumoral injection of micromolecule imiquimod hydrochloride with a dose of 6 mg/kg, followed by radiotherapy with 1.5 Gy on Day 0, 1, 2, 3, and 4 after administration, and the tumor on the left side of the mice was not subject to any treatment;

Group 4: The in-situ tumor was subject to intratumorally injected with the PLGA nano-particles of imiquimod (with a particle size of around 100 nm) with a dose of 6 mg/kg, followed by radiotherapy with 1.5 Gy on Day 0, 1, 2, 3, and 4 after administration, and the distal tumor in mice was not subject to any treatment;

Group 5: The mice were intratumorally injected with imiquimod microparticles (the present formulation) with a dose of 6 mg/kg, followed by radiotherapy with 1.5 Gy on Day 0, 1, 2, 3, and 4 after administration, and the distal tumor in mice was not subject to any treatment;

Group 6: The mice were intratumorally injected with imiquimod microparticles (the present formulation) with a dose of 12 mg/kg, followed by radiotherapy with 1.5 Gy on Day 0, 1, 2, 3, and 4 after administration, and the distal tumor in mice was not subject to any treatment;

The length and width of the in-situ tumor and the distal tumor were measured with vernier caliper every two days, and the volume of tumor was calculated as follows: $(\text{length}\times(\text{width})^2)/2$.

Figure 5:
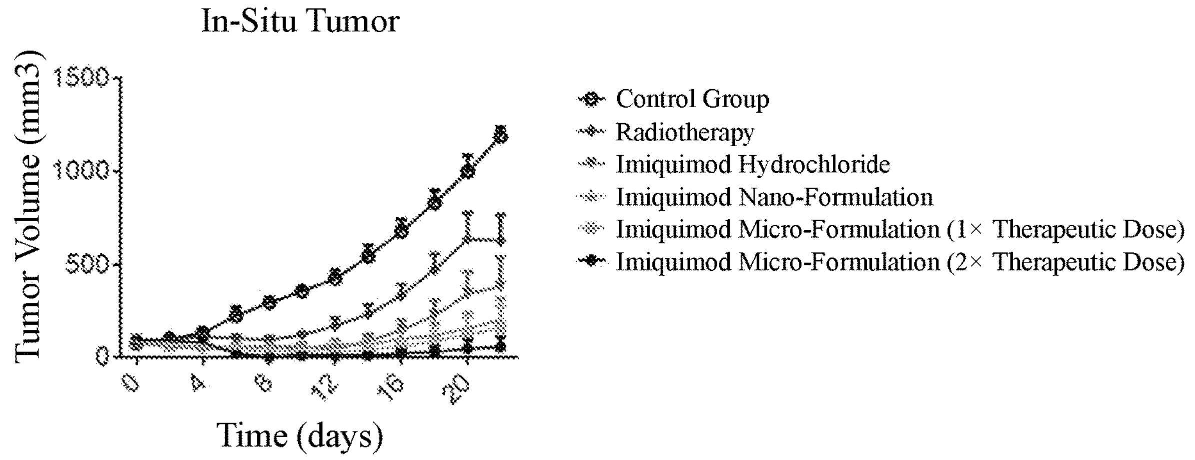
FIG. 5 is a comparison diagram showing the growth curves of in-situ tumors after injection of imiquimod formulations with different morphologies into a tumor, followed by radiotherapy.
Figure 6:
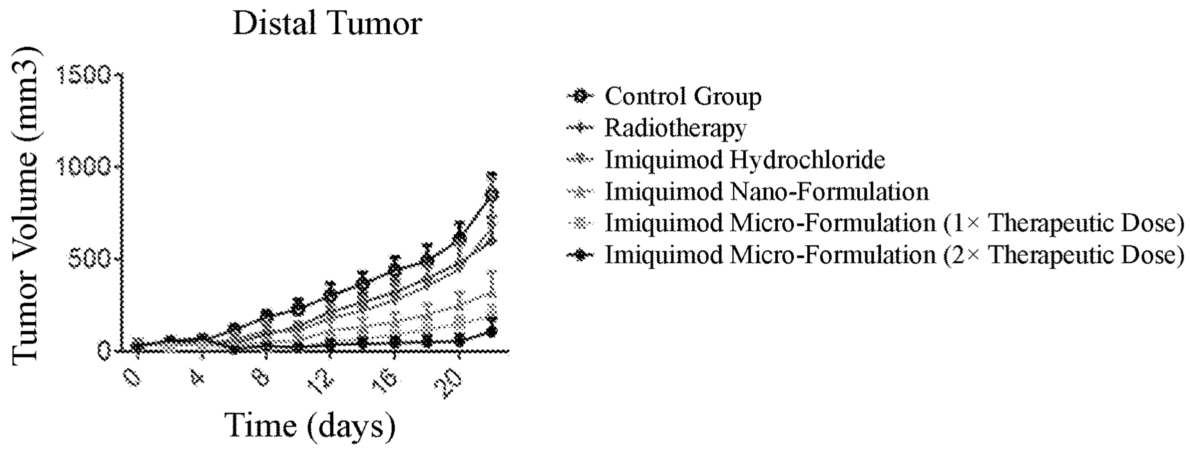
FIG. 6 is a comparison diagram showing the growth curves of distal tumors after injection of imiquimod formulations with different morphologies into a tumor, followed by radiotherapy.

FIG. 5 is a comparison diagram showing the grow curve of the in-situ tumor after intratumoral injection of the hydrochloride, nano-particles, and microparticles of Imiquimod, followed by radiotherapy, and FIG. 6 is a comparison diagram showing the grow curve of the distal tumor after intratumoral injection of the hydrochloride, nano-particles, and microparticles of Imiquimod, followed by radiotherapy.

Figure 7:
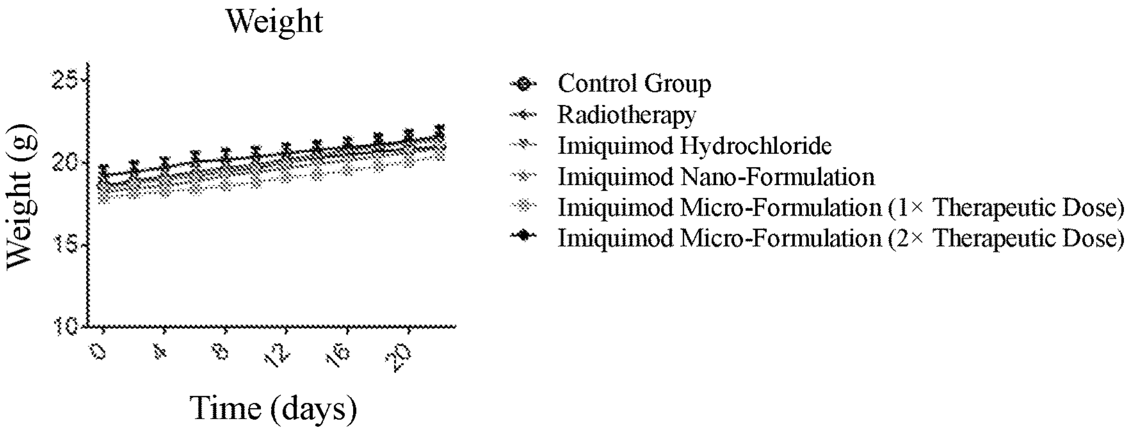
FIG. 7 is a comparison diagram showing the weight changes in mice after injection of imiquimod formulations with different morphologies into a tumor, followed by radiotherapy.

Therapeutic effect: it can be seen the growth curve of the in-situ tumor (FIG. 5) and the growth curve of the distal tumor (FIG. 6) that both the in-situ tumor and the distal tumor of mice in Group 6 have been effectively inhibited to almost stop growing, and thus it has a very good application prospect and value. In other corresponding therapeutic groups, some have a certain therapeutic effect, while some experimental groups have very limited therapeutic effect. The curves of weight change in mice of all the groups are shown in FIG. 7, which all fall within a normal range. There is no weight difference between the mice of experimental groups and the mice of control groups, indicating that the present formulation has certain safety.

Although it has been reported that radiotherapy can induce an abscopal effect, such effect is not very significant. In experiments, we found that injecting an immune adjuvant into a tumor, followed by radiating the tumor with rays can effectively enhance an immunogenic cell death induced by radiotherapy. On the one hand, it can produce an effect of improving the therapeutic effect of radiotherapy on the in-situ tumor; and on the other hand, it can provide a stronger abscopal effect to inhibit the growth of the distal tumor which is not radiated.

Example C4

The effect of this example for use in therapy in combination with microwave ablation was as follows:

Experimental method: Mice were transplanted with mouse colon tumor on the left and the right sides of the back in mice (one on the right side was deemed an in-situ tumor, and the other on the left side was deemed a distal tumor). The tumor-bearing mice were divided into 3 groups with 5 mice in each group for the therapeutic experiments of radiotherapy in combination with immunotherapy.

Group 1: The tumor in mice was not subject to any treatment, whether by drug injection or microwave treatment;

Group 2: The in-situ tumor in mice was subject to microwave thermal ablation alone with a microwave power of 7 W and a local tumor temperature of up to 53° C., while the tumor on the left side was not subject to any treatment;

Group 3: The tumor on the right side of mice was intratumorally injected with imiquimod microns formulation with a dose of 6 mg/kg, followed by microwave thermal ablation after administration with a microwave power of 7 W and a local tumor temperature of up to 53° C.; while the tumor on the left side of mice was not subject to any treatment;

The length and width of the in-situ tumor and the distal tumor were measured with vernier caliper every two days, and the volume of tumor was calculated as follows: $(\text{length}\times(\text{width})^2)/2$.

Figure 8:
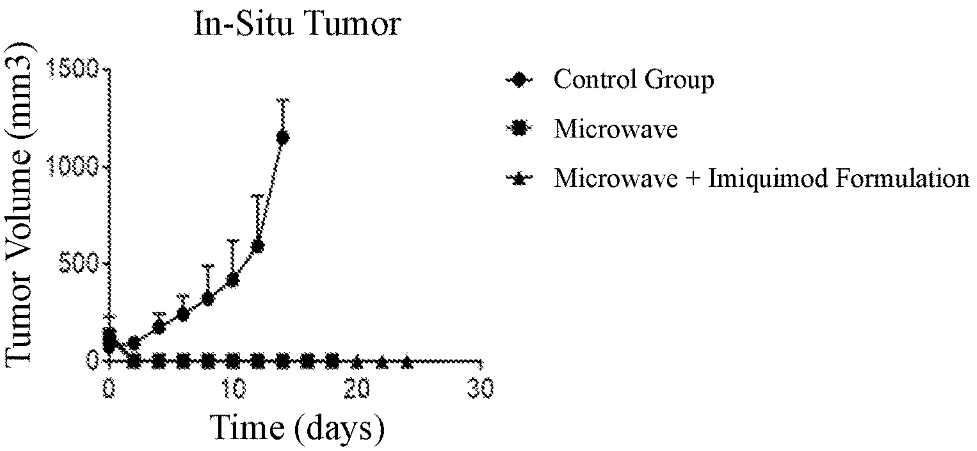
FIG. 8 is a graph showing the growth curve of an in-situ tumor in mice after injection of imiquimod microparticles into a tumor, followed by microwave ablation therapy.
Figure 9:
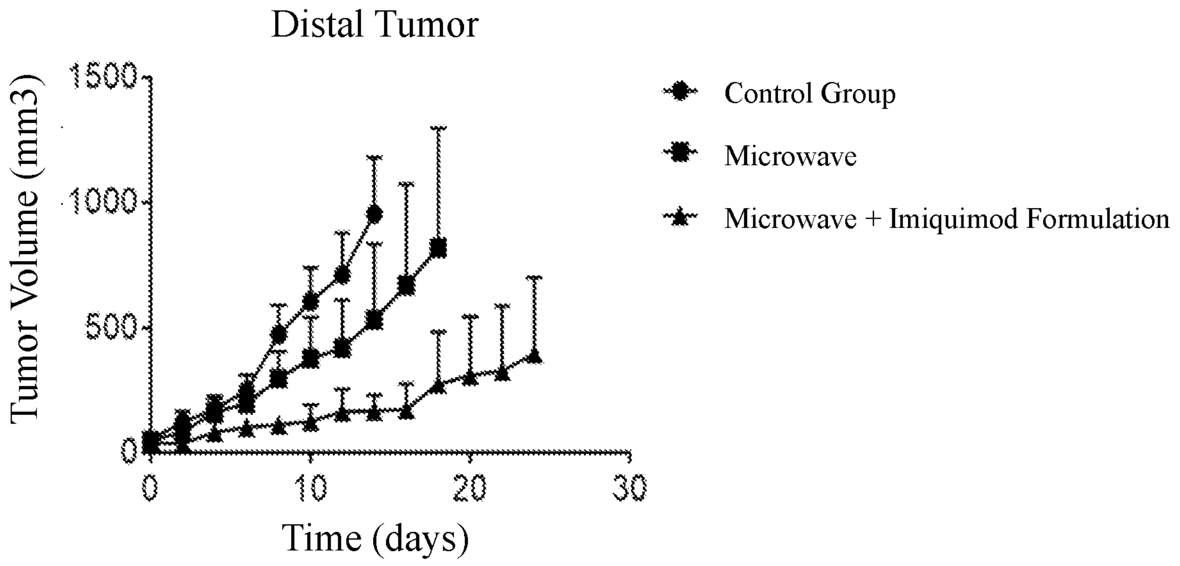
FIG. 9 is a graph showing the growth curve of a distal tumors in mice after injection of imiquimod microparticles into a tumor, followed by microwave ablation therapy.

Therapeutic effect: It can be seen from the growth curve of the in-situ tumor (FIG. 8) and the growth curve of the distal tumor (FIG. 9) that the tumors on both sides of the mice of Group 3 are well inhibited, but in the mice treated by microwave thermal ablation alone, only the in-situ tumor is eradicated, while the distal tumor is still growing, indicating that the imiquimod micro-formulation of the present application significantly improves the abscopal effect of the microwave thermal ablation therapy.

Example C5

The effect of this example for use in tumor chemotherapy in combination with immunotherapy was as follows:

Experimental method: Mice were transplanted with mouse colon CT26 tumor on the left and the right sides of the back in mice (one on the right side was deemed an in-situ tumor, and the other on the left side was deemed a distal tumor). The tumor-bearing mice were divided into 3 groups with 5 mice in each group for the therapeutic experiments of chemotherapy in combination with immunotherapy.

Group 1: The in-situ tumor in mice was intratumorally injected with normal saline, while the distal tumor was not subject to any treatment;

Group 2: The in-situ tumor in mice was intratumorally injected with oxaliplatin chemotherapeutic, while the distal tumor was not subject to any treatment;

Group 3: The in-situ tumor in mice was intratumorally injected with a mixture of oxaliplatin chemotherapeutic and imiquimod micro-formulation, while the distal tumor was not subject to any treatment;

The length and width of the tumor in mice were regularly measured, and the volume of tumor was calculated as follows: $(\text{length}\times(\text{width})^2)/2$.

Figure 10:
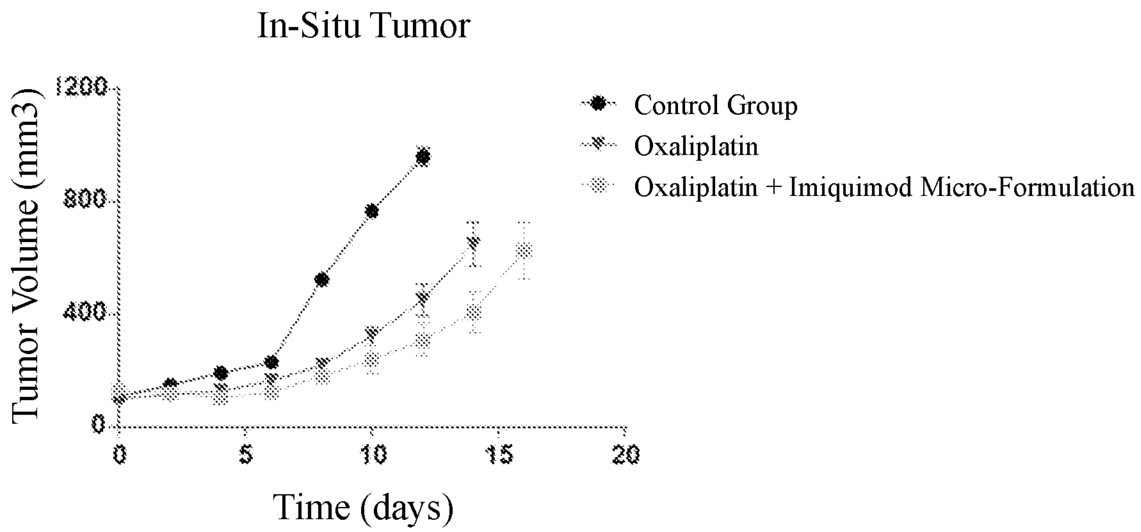
FIG. 10 is a graph showing a growth curve of an in-situ tumor in mice after tumor chemotherapy synergized with imiquimod microparticles.
Figure 11:
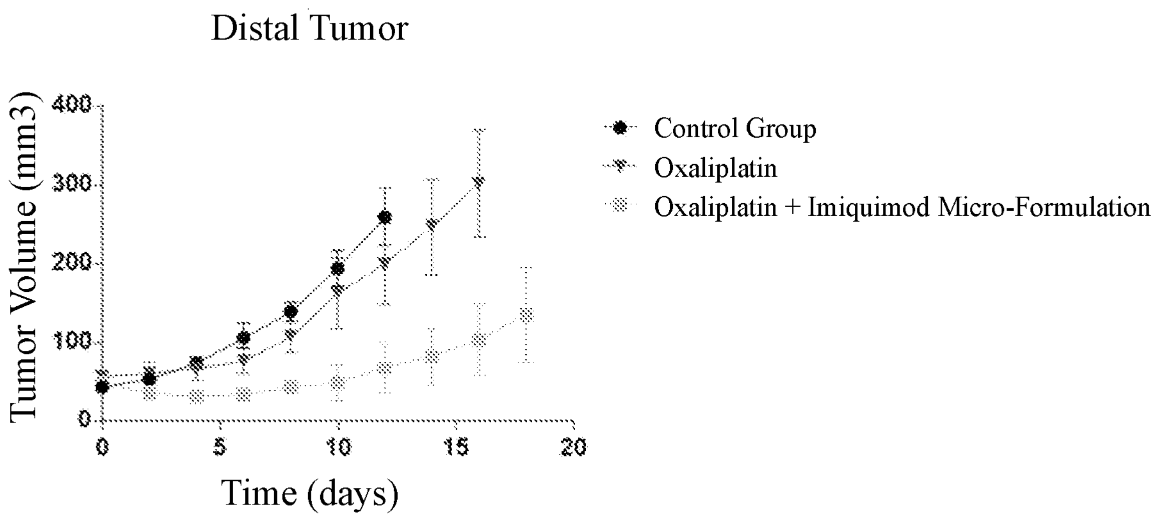
FIG. 11 is a graph showing a growth curve of a distal tumor in mice after tumor chemotherapy synergized with imiquimod microparticles.
Figure 12:
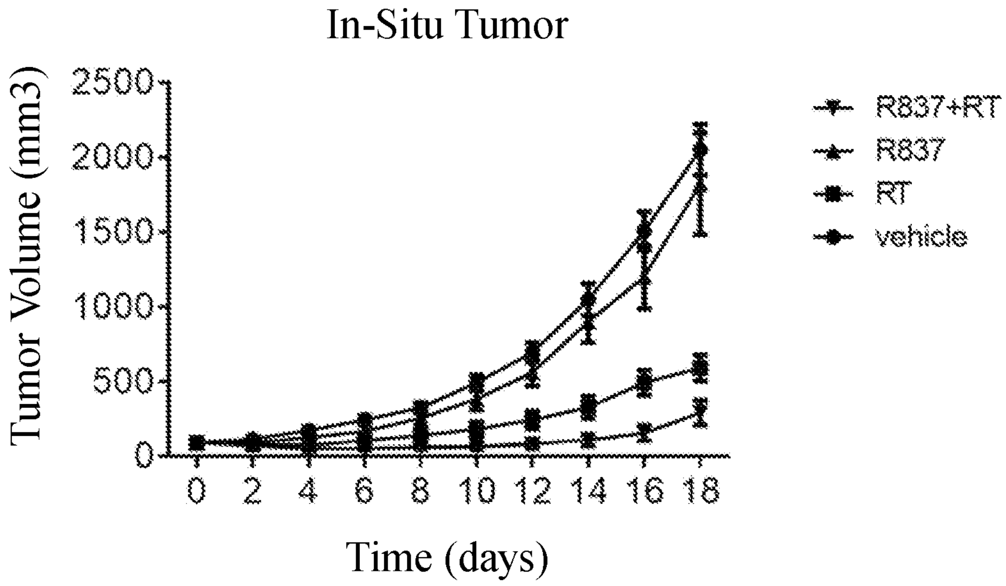
FIG. 12 is a graph showing a growth curve of an in-situ tumor in mice of different groups in an experiment micron-sized imiquimod suspension in combination with radiotherapy.
Figure 13:
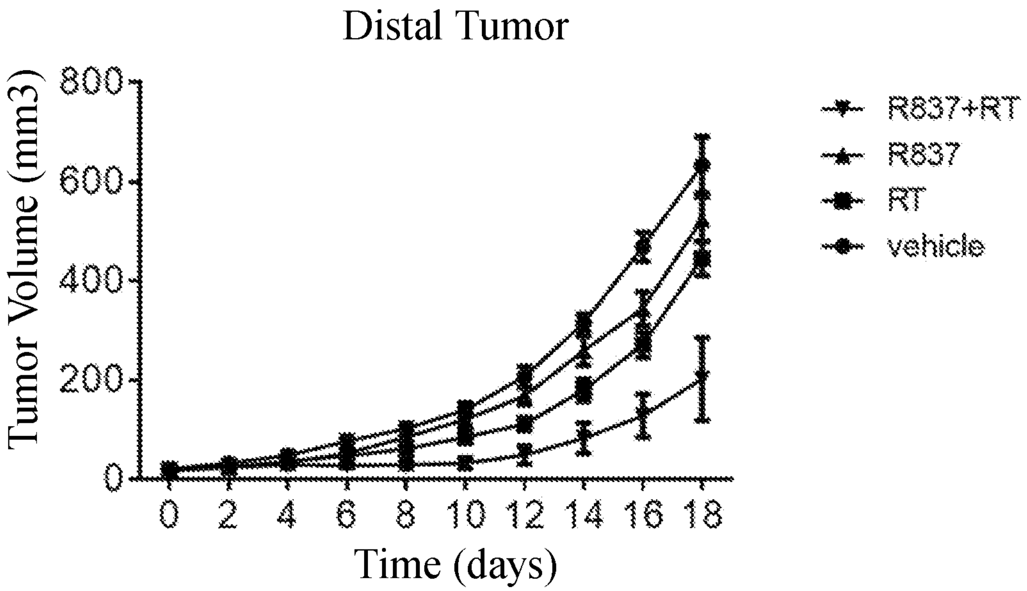
FIG. 13 is a graph showing a growth curve of a distal tumor in mice of different groups in an experiment of micron-sized imiquimod suspension in combination with radiotherapy.

Therapeutic effect: It can be seen from the growth curve of the in-situ tumor (FIG. 10) and the growth curve of the distal tumor (FIG. 11) that using chemotherapeutics can inhibit the growth of in-situ tumors, but does not produce significant inhibitory effect on the growth of distal tumors. By incorporating the imiquimod micro-formulation, the growth of the distal tumor can be effectively inhibited, indicating that the imiquimod micro-formulation of the present application can effectively enhance the abscopal effect of chemotherapy.

Example D. Animal Experiments

Example D1: Distributions in Organism

Mice were inoculated with CT26 tumor cells on their back to establish a CT26 subcutaneous tumor model of mice. Mice with the same tumor size were equally divided to 3 groups with 3 mice in each group. The grouping situation was as follows:

PLGA-R837: PLGA nano-particles loaded with R837;

R837·HCl: An aqueous solution of R837 hydrochloride in which R837 had an excellent dispersibility;

Imiquimod suspension formulation: A terminally sterilized imiquimod micron-sized suspension of the present application (with a suspending agent of lecithin).

According to the grouping, the mice in each group were intratumorally injected with different formulations containing the same dose of R837. In line with general method, the pharmacokinetic characteristics thereof were studied within 72 h after the injection to count the peak time ($T_{max}$), peak concentration ($C_{max}$) and half-life ($t_{1/2}$) of the drug concentration in the mouse blood in different groups. The results are shown in Table 13.

$C_{max}$ and $T_{max}$ reflect the rate of drug absorption from a certain formulation into the systemic blood circulation. The three formulations have the same peak time ($T_{max}$), but the R837 coated within PLGA nano-particles are largely exposed in blood soon, while the micron-sized imiquimod suspension formulation intratumorally injected does not show large exposure of drug in a short time. In addition, the half-life in blood circulation of the three formulations is different from each other. As compared with the nano-formulation and the micromolecule formulation, the micron micron-sized imiquimod suspension has a substantially prolonged half-life, that is, the intratumoral administration of the micron-sized imiquimod suspension has a significant sustained release effect.

TABLE 13

Statistical Chart Of Mean Pharmacokinetic Parameters Of Mice In Different Groups

| Group | $T_{max}$ (h) | $C_{max}$ (ng/mL) | $AUC_{all}$ (h * ng/mL) | $t_{1/2}$ |
|---|---|---|---|---|
| PLGA-R837 | 0.5 | 67.3 | 537 | 24 |
| R837•HCl | 0.5 | 17.35 | 140 | 7.7 |
| Micron-sized imiquimod suspension | 0.5 | 25.8 | 613 | 40 |

In theory, the long-term retention of the immune adjuvant in the tumor can more effectively irritate the antitumor immune response. To demonstrate the antitumor immune-enhancing effect of the sustained release dosage form, experiments were designed to verify the application of the micron-sized imiquimod suspension in the extratumoral radiotherapy or ethanol ablation therapy in combination with immunotherapy.

Example E. Radiotherapy and Ethanol Ablation Synergized with Micron-Sized Imiquimod Suspension

Example E1: Experiment of Treatment By Micron-Sized Imiquimod Suspension Formulation In Combination With Radiotherapy Mice were inoculated with CT26 colon cancer tumor cells on their back to establish a colon cancer subcutaneous dual-tumor model of mice, wherein the tumors were an in-situ tumor and a distal tumor, respectively. When the volume of the in-situ tumor reached about 100 $mm^3$, the mice were randomly divided to 6 groups. The grouping was as follows:

Vehicle: A vehicle control group, in which the in-situ tumor was subject to an intratumoral injection of a dispersing medium with an injection volume of 25 μL;

RT: An external radiation therapeutic group, in which the in-situ tumor was subject to X-ray radiation treatments with a radiation dose of 4 Gy, beginning at Day 0 and Day 3 from the treatment, respectively;

R837: An imiquimod micron-sized suspension formulation of the present application with a R837 concentration of 6 mg/mL and an injection dose of 25 μL;

R837+RT: An in-situ tumor was subject to intratumoral injection with 25 μL of imiquimod micron-sized suspension formulation at 6 mg/mL, followed by the same X-ray radiation treatment as the RT group.

In the group of R837+RT, the in-situ tumor in each mouse was subject to external radiation treatment at half an hour after the in-situ tumor was subject to intratumoral injection of the imiquimod suspension formulation, while the distal tumor was not subject to any treatment. The mice were monitored for the volumes of the in-situ tumor and the distal tumor, and a tumor growth curve was plotted. The results are shown in Table 14. Table 14 is a statistical chart of tumor inhibition rate of the in-situ tumor and the distal tumor. In accordance with the Jin's Formula: q=E (A+B)/(EA+EB−EA*EB), a drug synergy was calculated, wherein E (A+B) is the tumor inhibition rate of the group of the combinational treatment, and EA and EB each are the tumor inhibition rates of the two means used alone; and qq≥1 indicates that the two means have a synergistic effect. It can be calculated that the q value of the in-situ tumor is 1.17, and the q value of the distal tumor is 1.63, indicating both of them have a synergistic effect.

At the same time, it can be seen that a plurality of radiotherapies can inhibit the tumor growth to an extent, and the intratumoral injection of the imiquimod can further improve the therapeutic effect of tumor radiotherapy. The micron-sized imiquimod suspension formulation stimulates the strongest systemic antitumor immune response due to the long retention at the tumor side and the high bioavailability in vivo, and inhibits the growth of the distal tumor, which achieves a synergistic effect with the external radiation treatment.

TABLE 14

Tumor Inhibition Rate Of Imiquimod Suspension Formulation In Combination With Radiotherapy For Treatment Of Subcutaneous Tumor Mode At Endpoint Of Treatment.

| Group | Vehicle Control Group | RT | R837 | RT + R837 |
|---|---|---|---|---|
| In-situ tumor | 0 | 71.15% | 38.73% | 96.44% |
| Distant tumor | 0 | 29.67% | 17.23% | 68.14% |

In summary, the micron-sized imiquimod suspension formulation can be combined with the external radiation treatment to improve the antitumor immune response in vivo, especially to amplify the abscopal effect in radiotherapy to inhibit the growth of the distal tumor.

Example E2: Experiment of Treatment by Micron-Sized Imiquimod Suspension Formulation in Combination with Ethanol Ablation Ethanol ablation is one of local chemical ablation therapies for tumors, which involves injecting an absolute alcohol into the tumor to coagulate and necrotize the tumor tissue, thereby achieving the goal of treatment. However, a tumor is difficult to completely eradicate merely by means of chemical ablation such as injection of alcohol or hydrochloride acid with a dose that would not affect the peripheral normal tissues. In this example, using the micron-sized imiquimod suspension formulation in combination with ethanol ablation therapy demonstrates the antitumor effect of the micron-sized imiquimod suspension formulation of the present application in combination with chemotherapy.

First, a subcutaneous tumor model in mice was established. In particular, mice were inoculated with tumor cells on their back. Once the tumors grew to a volume of 100 $mm^3$, the mice were randomly divided into 5 groups with 5 mice in each group. The grouping was as follows:

Control: A blank control group;

R837: Peritumoral injection with the micron-sized imiquimod suspension;

ETOH: Intratumoral injection with absolute ethanol;

ETOH+R837 (25): Peritumoral injection with 25 μL of the micron-sized imiquimod suspension, and intratumoral injection with absolute ethanol;

ETOH+R837 (50): Peritumoral injection with 50 μL of the imiquimod suspension, and intratumoral injection with absolute ethanol.

Figure 14:
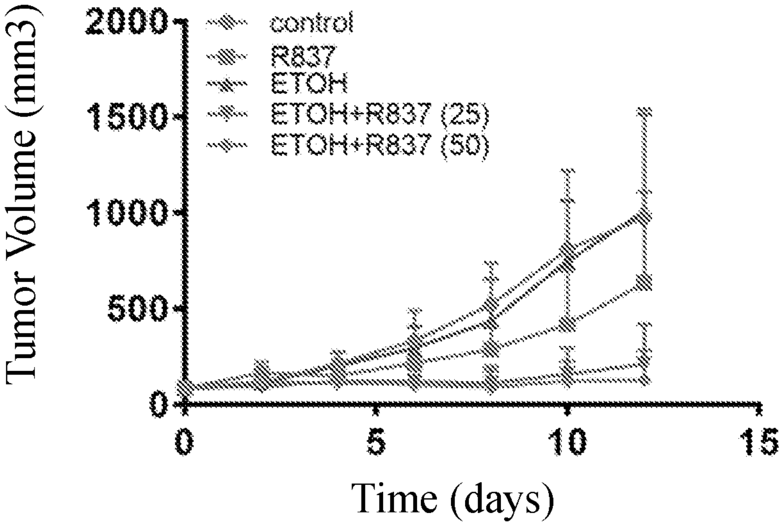
FIG. 14 is a graph showing a growth curve of a tumor in mice of different groups in an experiment of micron-sized imiquimod suspension in combination with ethanol ablation therapy.

Of those, the micron-sized imiquimod suspension had a concentration of 12 mg/mL, and the absolute ethanol had an injection dose of 30 μL. In the combinational therapeutic group, the micron-sized imiquimod suspension formulation was first injected to the subcutaneous site around the tumor, and after an interval of around 10 minutes, the absolute ethanol was then administered in a manner of intratumoral injection. The mice were monitored for the changes in tumor volumes, and the curves of tumor growth were plotted. The results are shown in FIG. 14.

In the experiments, it was found that the mice in the group of absolute ethanol alone showed tumor fibrosis and scabbing at the center of the tumor. However, because the peripheral tumor tissues were not be completely eradicated and subsequently developed gradually, so that the outer diameter continued to increase, resulting that the tumor volumes in this group were not highly different from those of the control group. Thus, among the growth curves of tumor, the growth curves of tumor are almost coincided in the ethanol ablation group and the blank control group. In addition to this special case, it can be seen from FIG. 14 that the tumor growth of mice in the group of the micron-sized imiquimod suspension in combination with ethanol ablation was obviously inhibited. Administration of the micron-sized imiquimod with different doses can improve the therapeutic effect of ethanol ablation, achieve a better tumor treatment effect and inhibit the tumor growth, indicating that the micron-sized imiquimod suspension can enhance the therapeutic effect of ethanol ablation on tumors.

Example F. Imiquimod Suspension can Help to Achieve a Sustained Release of a Platinum-Based Chemotherapeutic Drug, Enhancing the Effect of Antitumor Immune Response Caused by the Immunogenic Cell Death

Example F1: Verification of Sustained Release Effect of Use of Oxaliplatin Mixed with Imiquimod Suspension on Oxaliplatin Mice were inoculated with colon cancer (CT26) tumor cells on the back of the tumor in mice to establish a subcutaneous tumor model in mice. About 1 week after the formation of lump at the inoculated site, the mice were randomly divided into two groups, which were, respectively:

OXA: An oxaliplatin solution

OXA-R837: An oxaliplatin solution mixed with the micron-sized imiquimod suspension Correspondingly, the mice in each group were intratumorally injected with the oxaliplatin solution or the oxaliplatin solution mixed with the micron-sized imiquimod suspension formulation, sampled for blood at different time points (10 min, 30 min, 1 h, 3 h, 6 h, 9 h, 12 h, 24 h, 48 h, 72 h), and sacrificed at the end point to collect main organs and tumors for detecting the relative contents of platinum ions in the blood samples and organs by ICP-MS and plotting a statistical diagram. The results are shown in FIG. 15 and FIG. 16.

Figure 15:
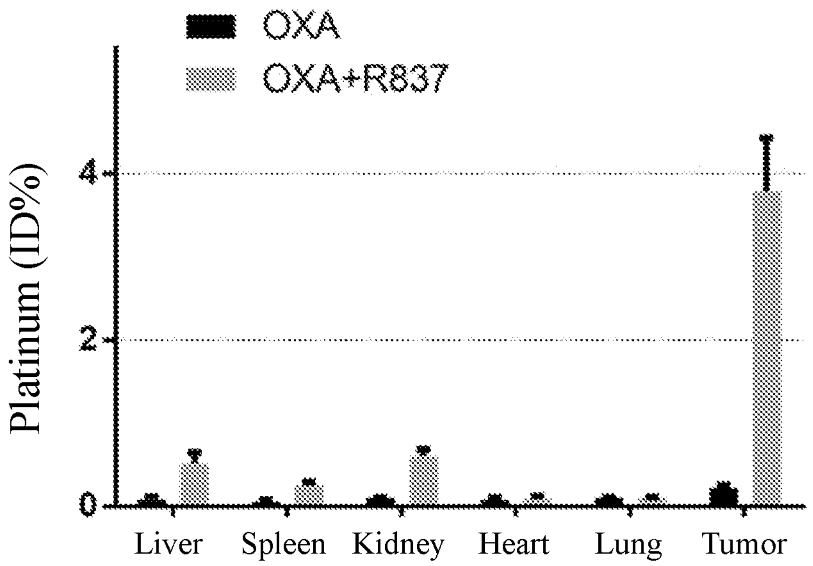
FIG. 15 is a statistical diagram of the relative platinum contents in main tissues and organs before and after mixing oxaliplatin with a micron-sized imiquimod suspension, and 72 h after intratumoral injection.

FIG. 15 shows the biological distribution status of oxaliplatin. As compared with the free oxaliplatin, administration by premixing with the imiquimod micron-sized suspension can remarkably increase the retention amount of the platinum-based drug in the tumor site. At 72 h after drug injection, in the mixed injection group, the platinum content in the tumor site in mice is tens of times than those in the free drug group, indicating that the imiquimod micron-sized suspension can increase the retention of the platinum-based chemotherapeutic drug in the tumor site, and slowing down the release of oxaliplatin.

Figure 16:
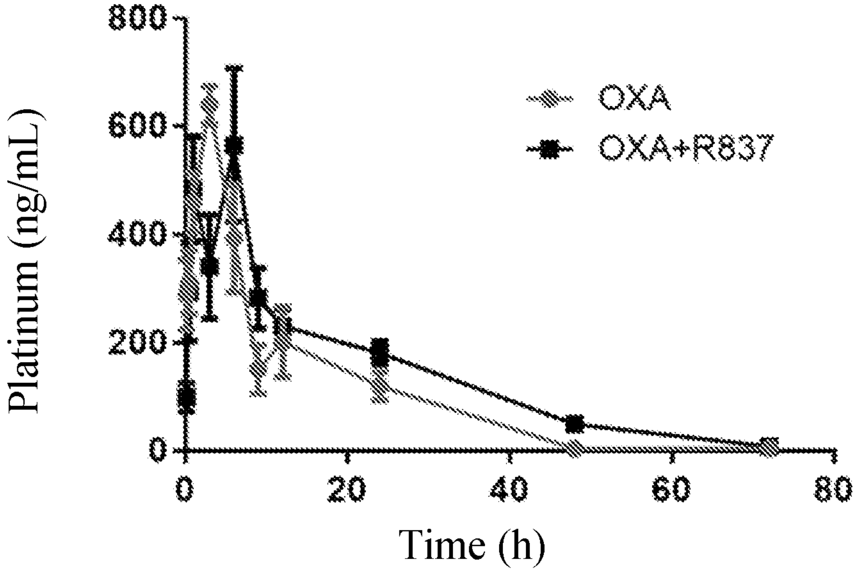
FIG. 16 is a graph showing a curve of drug concentration in blood with time before and after mixing oxaliplatin with a micron-sized imiquimod suspension, and after intratumoral injection.

FIG. 16 shows the status of the concentration of oxaliplatin in blood with time. As compared with the free oxaliplatin drug solution, the oxaliplatin mixed with the micron-sized imiquimod suspension has more obvious sustained release, which is particularly manifested in lower peak concentration, later peak time, and longer retention time in blood. The particular peak times (Tmax), peak concentrations (Cmax) and areas under curve (AUC) are shown in Table 14. After mixed with a micron-sized imiquimod suspension, the exposure time of oxaliplatin in the circulation system is prolonged so that the bioavailability of oxaliplatin is increased.

TABLE 14

| Pharmacokinetic Data of Oxaliplatin | | | |
|---|---|---|---|
| Group | $T_{max}$ (H) | $C_{max}$ (Ng/G) | $AUC_{all}$ |
| OXA | 3 | 638.685 | 7850.866 |
| OXA + R837 | 6 | 565.728 | 10438.525 |

Example F2: Oxaliplatin in Combination with Micron-Sized Imiquimod Suspension Formulation Synergizing the Antitumor Effect Mice were inoculated with different amounts of colon cancer (CT26) tumors on both sides of the back in mice (the inoculated amount on the left side was ⅕ of that on the right side) to establish a subcutaneous two-sided tumor model, wherein the tumor on the right side was deemed an in-situ tumor, and that on the left right was deemed a distal tumor. Once the in-situ tumors reached a size of about 100 $mm^3$, the mice were randomly divided into 4 groups, which were treated respectively. The grouping was as follows:

VEHICLE: A vehicle group, in which 30 μL of normal saline was injected.

OXA: 30 μL of the oxaliplatin solution was injected.

R837: 30 μL of the micron-sized imiquimod suspension was injected.

OXA+R837: 30 μL of the mixed solution of the micron-sized imiquimod suspension and oxaliplatin was injected.

Figure 17:
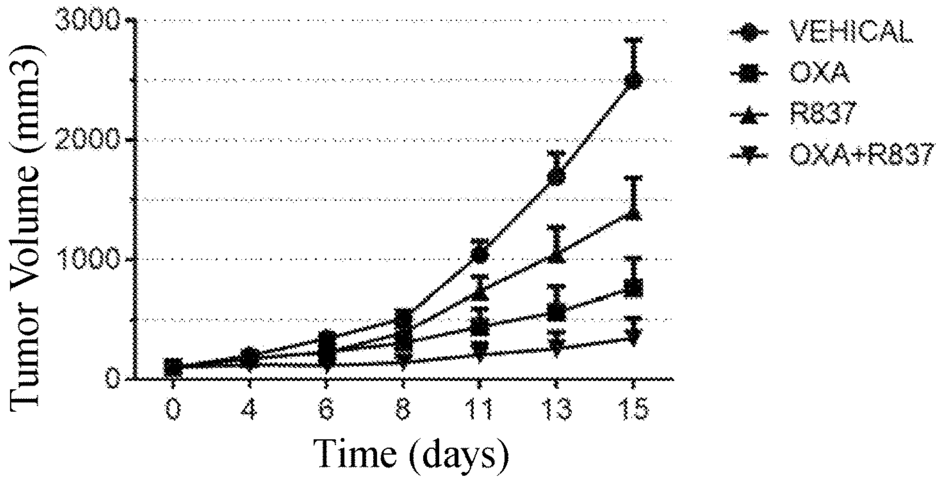
FIG. 17 is a graph showing a tumor growth curve of an in-situ tumor in a two-sided tumor model of mice with groups including a vehicle control group, a therapeutic group of oxaliplatin alone, a therapeutic group of imiquimod suspension formulation, and a therapeutic group of oxaliplatin in combination with imiquimod suspension formulation.

On Day 1 of the treatment, the in-situ tumor was administered by intratumoral injection, wherein the concentration of oxaliplatin was 4 mg/mL, and the concentration of imiquimod was 6 mg/mL. After administration, the tumor volume in mice was recorded to plotted a growth curve of ice. The results are shown in FIG. 17 (the growth curve of the in-situ tumor) and FIG. 18 (the growth curve of the distal tumor). FIG. 17 shows the growth curve of the in-situ tumor in mice. As calculated, the tumor inhibition rate of the therapeutic groups is shown in Table 15.

TABLE 15

| Tumor Inhibition Rate of Different Groups on Day 15 After Treatment | | | | |
|---|---|---|---|---|
| Group | VEHICAL | OXA | R837 | OXA + R837 |
| In-situ tumor | 0 | 69.56% | 43.94% | 86.26% |
| Distant tumor | 0 | 41.87% | 22.94% | 69.95% |

In accordance with the Jin's Formula: q=E (A+B)/(EA+EB−EA*EB), a drug synergy was calculated, wherein E (A+B) is the tumor inhibition rate of the group of the combinational treatment, and EA and EB each are the tumor inhibition rates of the two components used alone; and qq≥1 indicates that the two components have a synergistic effect. As calculated, the q of the tumor inhibition rate is about 1.1 in the in-situ tumor and about 1.27 in the distal tumor, indicating that the micron-sized imiquimod suspension has an effect of synergizing the oxaliplatin chemotherapy.

Figure 18:
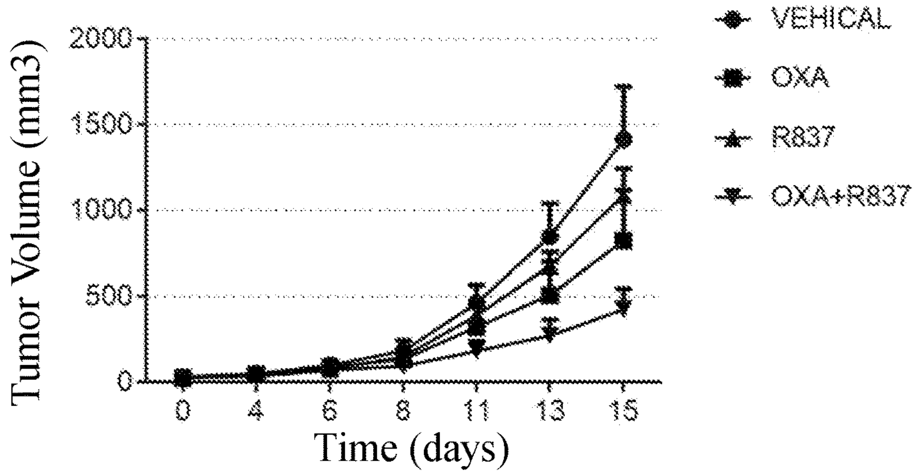
FIG. 18 is a graph showing a tumor growth curve of a distal tumor in a two-sided tumor model of mice with groups including a vehicle control group, a therapeutic group of oxaliplatin alone, a therapeutic group of imiquimod suspension formulation, and a therapeutic group of oxaliplatin in combination with imiquimod suspension formulation.

At the same time, the oxaliplatin can result in the immunogenic death of tumors, and the addition of imiquimod can enhance the antitumor immune effect, causing a systemic antitumor immune response to inhibit the growth of distal tumor. Compared with individual components alone, simultaneous intratumoral injection of oxaliplatin and imiquimod can effectively inhibit the growth of distal tumor. As shown in FIG. 18, the mice in the combinational therapeutic group showed the slowest tumor growth and a less intra-group difference.

Example G. Investigation of Sustained-Release Effect of Imiquimod Micron-Sized Suspension Formulation on Anthracycline-Based Chemotherapeutic Drug

Example G1: Experiment of In-Vitro Release of Doxorubicin After the Imiquimod Micron-Sized Suspension Formulation Was Mixed With Doxorubicin (DOX)

Grouping and Preparation of Samples:

DOX: An aqueous solution of doxorubicin with a concentration of 3 mg/mL;

DOX+R837: 3 mg of doxorubicin dissolved in 1 mL of the imiquimod micron-sized suspension formulation (a lecithin-containing and sterilized sample, wherein the concentration of imiquimod is 12 mg/mL).

Figure 19:
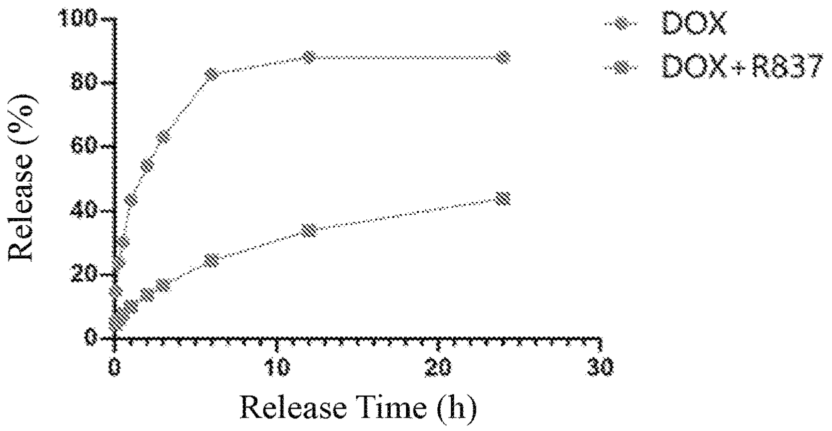
FIG. 19 is a graph showing an in-vitro release curve of doxorubicin mixed with a micron-sized imiquimod suspension formulation.

Specific experimental steps: The formulated solutions of various groups were added into dialysis bags (with a molecular weight cut-off of 3500D) which were placed in 500 mL of PBS solution for dialysis. At different points of time, the dialysate was detected for the drug concentrations by means of detecting the UV absorbance in the wave band where the drug was located. The drug content was calculated, and compared with the initial drug content to plot a curve of change in the relative drug content of different sample dialysates. The results are shown in FIG. 19. Of those, after the micron-sized imiquimod suspension was mixed with doxorubicin, the drug release curve thereof was obviously slowed down, indicating that the micro-sized imiquimod suspension can significantly decrease the release rate of drug to achieve the sustained-release effect. The in-vitro simulation release experiment can reflect the in-vivo behavior of drug to an extent, indicating that the injection of the micron-sized imiquimod suspension premixed with doxorubicin can slow down the release rate of drug after in-situ injection, prolong the retention time of chemotherapeutic drugs in the tumor site, and increase the retention amount of drugs in the tumor site, thereby enhancing the action effect of drug in the tumor site and reducing the toxic and side effects of drugs on the system.

Example G2: Changing the Mixing Ratio of the Imiquimod Micron-Sized Suspension Formulation to the Doxorubicin to Verify the Sustained Release Effect Grouping and Preparation of Samples:

DOX: An aqueous solution of doxorubicin with a concentration of 3 mg/mL;

DOX+R837: Doxorubicin dissolved in the micron-sized imiquimod suspension formulation, wherein the concentration of the imiquimod suspension formulation was 12 mg/mL, and the final concentration of doxorubicin was 3 mg.

DOX+R837 (1/3): Doxorubicin dissolved in the micron-sized imiquimod suspension formulation, wherein the concentration of the imiquimod suspension formulation was 4 mg/mL, and the final concentration of doxorubicin was 3 mg.

Figure 20:
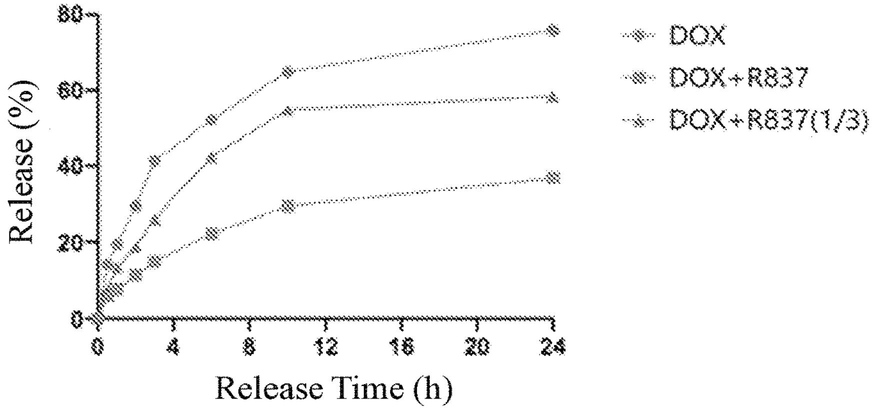
FIG. 20 is a graph showing in-vitro release curves of doxorubicin mixed with micron-sized imiquimod suspension formulations with different concentrations.

The drug release curves of the three groups were plotted by the same detection method and data processing method as those of Example G1. The results are shown in FIG. 20. After the amount of the imiquimod micron-sized suspension was reduced, the release rate of drug increases. However, as compared with the aqueous solution of doxorubicin alone, the release rate is still slowed down. It further indicates that the micro-sized imiquimod suspension formulation can slow down the release of doxorubicin, and the sustained-release effect is associated with the ratio therebetween. The higher the concentration of the micron-sized imiquimod suspension formulation, the better the sustained release effect. The concentration ratio of doxorubicin to imiquimod is 1:1 to 1:18.

Example G3: In-Vitro Release Experiment of Epirubicin (EPI) Mixed with Micron-Sized Imiquimod Suspension Formulation Grouping and Preparation of Samples:

EPI: An aqueous solution of epirubicin with a concentration of 2 mg/mL;

EPI+R837: Epirubicin dissolved in the micron-sized imiquimod suspension formulation, wherein the final concentration of epirubicin was 2 mg.

Figure 21:
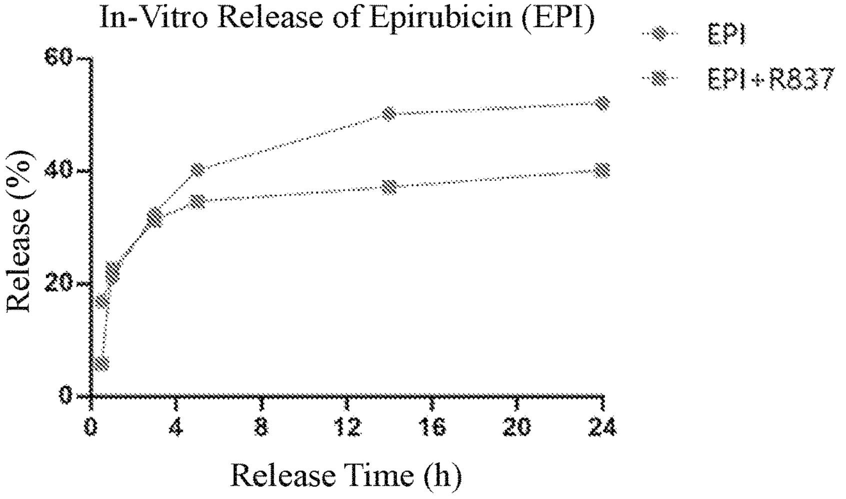
FIG. 21 is a graph showing an in vitro release curve of epirubicin mixed with a micron-sized imiquimod suspension formulation.

As in Example G1, the sample was placed into a dialysis bag (with a molecular weight cut-off of 3500D) with a sustained-release system of 500 mL of PBS solution. The drug release amount was detected at different points of time to calculate the release percentage and plot the release curve of drug. The results are shown in FIG. 21. The results show that, in the early stage of the in vitro release experiment (before 6 h), the drug release trends are similar in different groups. However, with the extension of time, the release of epirubicin mixed with the micron-sized imiquimod suspension formulation slow down.

As compared with the sustained-release effect of doxorubicin, the sustained-release effect of epirubicin is slightly lower. The inventors speculate that the anthracycline-based chemotherapeutic drugs in the mixed solution may form a certain π-π stacking force with the imiquimod microparticles, while doxorubicin and epirubicin are isomers of each other. From the analytical structure, doxorubicin is easy to form a more stable π-π stacking force with imiquimod, thereby showing a stronger sustained-release effect.

When the concentration of drug in relation to the suspension is too high, the excess drug is in a free state, and the portion of drug will be released quickly in a short time. However, as for the chemotherapeutic drugs stabilized by the π-π interaction with the imiquimod microparticles, the change in drug metabolism behavior thereof is associated with the micron-sized imiquimod particles. After intratumoral injection of the mixture, the chemotherapeutic drug has similar pharmacokinetics to the imiquimod microparticles, with the retention enhanced and the release slowed down.

Example G4: Sustained-Release Effect of Micron-Sized Imiquimod Suspension Formulation Obtained by Phosphatidyl Glycerol as Suspending Agent on Epirubicin Grouping and Preparation of Samples:

EPI: An aqueous solution of epirubicin with a concentration of 2 mg/mL;

EPI+R837 (0.25PG): Epirubicin dissolved in the micron-sized imiquimod suspension formulation obtained by phosphatidyl glycerol as suspending agent, wherein the mass ratio of phosphatidyl glycerol to imiquimod was 0.25:1, and the final concentration of epirubicin was 2 mg/mL;

EPI+R837 (3PG): Epirubicin dissolved in the micron-sized imiquimod suspension formulation obtained by phosphatidyl glycerol as suspending agent, wherein the mass ratio of phosphatidyl glycerol to imiquimod was 3:1, and the final concentration of epirubicin was 2 mg/mL.

Figure 22:
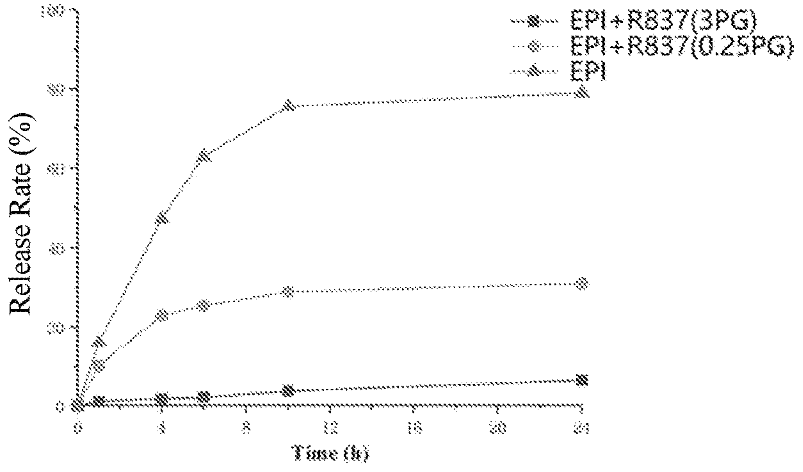
FIG. 22 is a graph showing an in vitro release curve of epirubicin mixed with a micron-sized imiquimod suspension which is suspended with phosphatidyl glycerol.

By a method like Example G1, the drug release was detected by dialysis experiment. The results are shown in FIG. 22. The drug dissolution rate of the epirubicin dissolved in the micron-sized imiquimod suspension formulation was significantly slowed down, and the drug release in 24 h was only around ¼ of that in the control group. When the proportion of phosphatidyl glycerol was increased, the drug release was slower. The negative charges on the surface of phosphatidyl glycerol formed an electrostatic interaction with the positive charges on the surface of epirubicin, thereby showing a stronger sustained-release effect.

The foregoing illustration of the disclosed examples enables persons skilled in the art to embody or use the present application. Various modifications to these examples are obvious for persons skilled in the art. The present application is not limited to the examples as shown herein, as long as it conforms to the principle and characteristics disclosed herein.

The invention claimed is:

1. A self-sustained release immune adjuvant suspension in preparation of a radiotherapy sensitizing agent or a thermotherapy sensitizing agent, the self-sustained release immune adjuvant suspension composed of a lipid soluble immune adjuvant comprising imiquimod and a surfactant with a higher fatty chain, the balance being a dispersing medium, wherein the imiquimod is coated with the surfactant to form imiquimod microparticles, the concentration of the imiquimod microparticles is 1 to 18 mg/mL, and a mass ratio of the surfactant with the higher fatty acid chain to the imiquimod microparticles is 0.025 to 1:1.

2. The self-sustained release immune adjuvant suspension according to claim 1, wherein the particles of the lipid soluble immune adjuvant are core-shell composite with a particle size of 0.5 to 5 microns.

3. The self-sustained release immune adjuvant suspension according to claim 1, wherein the surfactant with a higher fatty acid chain comprises an anionic surfactant; wherein the anionic surfactant comprises at least one of sodium oleate, sodium dodecyl sulfate, sodium stearate, sodium N-lauroyl sarcosinate, sodium cocoyl methyl taurate, sodium N-lauroyl glutamate, sodium lauryl polyoxyethylene ether carboxylate, and dodecyl phosphate; or, wherein the surfactant with a higher fatty acid chain comprises an amphiphilic ionic surfactant; or, wherein the surfactant with a higher fatty acid chain comprises a phospholipid ionic surfactant; wherein the phospholipid ionic surfactant comprises at least one of lecithin, soybean phospholipid, phosphatidylglycerol, phosphatidylethanolamine, phosphatidylserine, and phosphatidylinositol.

4. The self-sustained release immune adjuvant suspension according to claim 1, wherein a hydrophobic structural moiety of the surfactant comprises not less than 20 oxypropylene units; wherein the surfactant comprises at least one of Poloxamer 188, Poloxamer 237, Poloxamer 338, and Poloxamer 407.

5. The self-sustained release immune adjuvant suspension according to claim 1, wherein a hydrophobic structural moiety of the surfactant comprises one or more hydrocarbon chains with a total of not less than 15 carbon atoms; wherein the surfactant comprises at least one of sorbitan sesquioleate, soybean phospholipid, glyceryl monostearate, polysorbate 40, polysorbate 60, polysorbate 65, polysorbate 80, polysorbate 85, sorbitan stearate, stearate, vitamin E polyethylene glycol succinate, polyoxyethylene alkyl ether, polyoxyethylene stearate, polyoxyl (40) stearate, sucrose stearate, a polyoxyethylenated castor oil derivative, cetomacrogol 1000, and lecithin.

* * * * *